United States Patent [19]
Meyerowitz et al.

[11] Patent Number: 5,744,693
[45] Date of Patent: Apr. 28, 1998

[54] PLANTS HAVING ALTERED FLORAL DEVELOPMENT

[75] Inventors: Elliot M. Meyerowitz, Pasadena; Martin F. Yanofsky, San Diego, both of Calif.; Hong Ma, Huntington, N.Y.

[73] Assignee: California Institute of Technology, Pasadena, Calif.

[21] Appl. No.: 460,512

[22] Filed: Jun. 2, 1995

Related U.S. Application Data

[63] Continuation of Ser. No. 293,278, Aug. 19, 1994, abandoned, which is a continuation of Ser. No. 956,694, Oct. 2, 1992, abandoned.

[51] Int. Cl.⁶ .................. A01H 4/00; C12N 5/14; C12N 15/82
[52] U.S. Cl. .................. 800/205; 800/DIG. 15; 800/DIG. 17; 800/DIG. 43; 435/172.3; 435/240.4; 435/320.1
[58] Field of Search .................. 536/23.6; 435/172.3, 435/320.1, 240.4; 800/205, 230, DIG. 15, DIG. 17, DIG. 43

[56] References Cited

U.S. PATENT DOCUMENTS

| | | | |
|---|---|---|---|
| 5,034,323 | 7/1991 | Jorgensen et al. | 435/172.3 |
| 5,107,065 | 4/1992 | Shewmaker et al. | 800/205 |

FOREIGN PATENT DOCUMENTS

| | | |
|---|---|---|
| 0426641A2 | 5/1991 | European Pat. Off. |
| WO8700551 | 1/1987 | WIPO . |
| WO9011682 | 10/1990 | WIPO . |
| WO9012084 | 10/1990 | WIPO . |
| WO9109112 | 6/1991 | WIPO . |
| WO9113992 | 9/1991 | WIPO . |

OTHER PUBLICATIONS

Bowman, J. L., et al., *The Plant Cell* 3:749–758 (1991).
Bowman, J. L., et al., *Development* 112:1–20 (1991).
Meyerowitz, E., NIH Grant Proposal Awarded 6 Mar. 1991.
van der Krol, et al (1990) Plant Molecular Biology 14:457, Abstract.
Drews, et al (Jun. 14, 1991) Cell 65:991–1002.
Komari (Aug. 1990) Theor. Appl. Genet. 80:167–171.
Bowman, et al (May 1991) Development 112 (1): 1–20.
Yanofsky, et al. (5 Jul. 1990) Nature 346:35–39.

*Primary Examiner*—Che S. Chereskin
*Attorney, Agent, or Firm*—Flehr Hohbach Test Albritton & Herbert LLP; Richard F. Trecartin

[57] ABSTRACT

The invention includes plants having at least one cell transformed with a vector comprising at least a portion of an agamous nucleic acid. Such plants have a phenotype characterized by altered floral development such as an AG or AP2 phenotype. The invention also includes vectors comprising at least a portion of an agamous nucleic acid operably linked to a promoter other than the promoter naturally associated with the agamous nucleic acid. In an alternate embodiment, the vector comprises at least a portion of an agamous nucleic acid operably linked in an antisense orientation to a promoter. The invention also includes methods using such vectors for producing plants having altered floral development.

25 Claims, 17 Drawing Sheets
(7 of 17 Drawing(s) in Color)

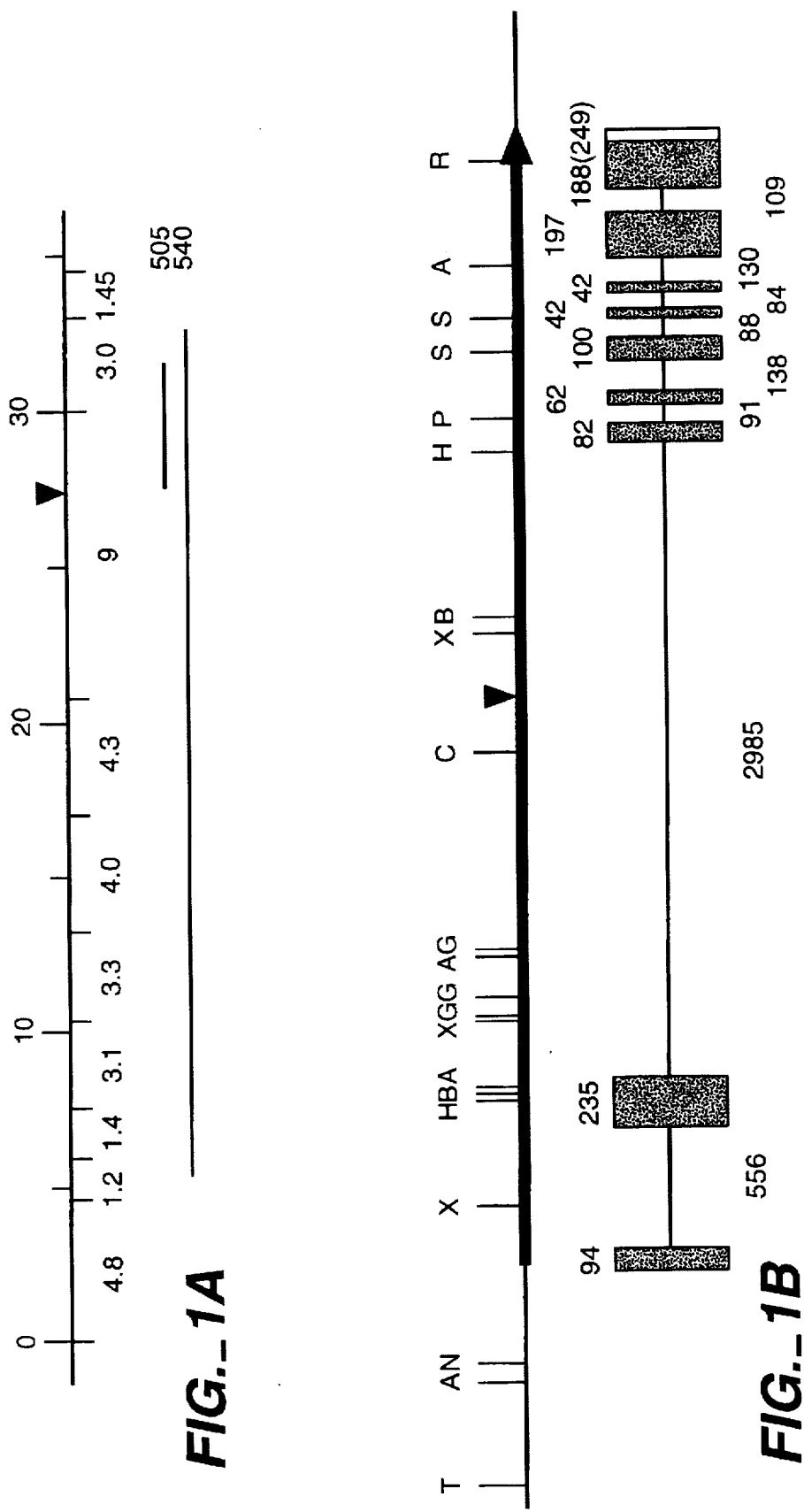
FIG._1A
FIG._1B

```
     CTAAATGTACTGAAAAGAAACACCAGTTAATTAATTATACTTTCCTCACATATAACTATCAACCAGTACAAAACTTTGTC
     AATTCTCAAAATCAACTTTCACCACCATATCTAATAATTATCTAACATGTGTATGTTCCAAAACCAGTTAAATGAATTACTTTTCAGAAA
     ATACATGTATATTAACTCTATCTAATAAAGAAGAAACATACTTATCTCATAGATTCATTCATAAAACTATGCTTAGTGA
     GTAAGAAACCAGTAATCAAACACAATTGACAGACACTATATGATGTAAAAGTGGGAAAATATGTGATAAATAGTAG
     AGAAAATTAAAAGAAAAATAATATTCCTTTATAAATGTATATACCATCTCTTCACCAGCACACAACCTTACTTCATTTC

1  CAT TTT CTG CAA CTT CTC CAA ATC TCA TAC TTT CCA GAA AAT CAT TTT CCC AAG
  1  His Phe Leu Gln Leu Leu Gln Ile Ser Tyr Phe Pro Glu Asn His Phe Pro Lys

55  AAA AAT AAA ACT TTC CCC TTT GTT CTT CTC CCC CCA ACA GCA ATC ACG GCG TAC
 19  Lys Asn Lys Thr Phe Pro Phe Val Leu Leu Pro Pro Thr Ala Ile Thr Ala Tyr

109  CAA TCG GAG CTA GGA GGA GAT TCC TCT CCC TTG AGG AAA TCT GGG AGA GGA AAG
 37  Gln Ser Glu Leu Gly Gly Asp Ser Ser Pro Leu Arg Lys Ser Gly Arg Gly Lys

163  ATC GAA ATC AAA CGG ATC GAG AAC ACA ACG AAT CGT CAA GTC ACT TTT TGC AAA
 55  Ile Glu Ile Lys Arg Ile Glu Asn Thr Thr Asn Arg Gln Val Thr Phe Cys Lys

217  CGT AGA AAT GGT TTG CTC AAG AAA GCT TAC GAG CTC TCT GTT CTC TGT GAT GCT
 73  Arg Arg Asn Gly Leu Leu Lys Lys Ala Tyr Glu Leu Ser Val Leu Cys Asp Ala

271  GAA GTC GCA CTC ATC GTT TTC TCT AGC CGT GGT CGT AAG TAC TCT AAC
 91  Glu Val Ala Leu Ile Val Phe Ser Ser Arg Gly Arg Leu Tyr Glu Tyr Ser Asn

325  AAC AGT GTA AAA GGT ACT ATT GAG AGG TAC AAG AAG GCA ATA TCG GAC AAT TCT
109  Asn Ser Val Lys Gly Thr Ile Glu Arg Tyr Lys Lys Ala Ile Ser Asp Asn Ser

379  AAC ACC GGA TCG GTG GCA GAA ATT AAT GCA CAG TAT TAT CAA CAA GAA TCA GCC
127  Asn Thr Gly Ser Val Ala Glu Ile Asn Ala Gln Tyr Tyr Gln Gln Glu Ser Ala
```

FIG._1C-1

```
433  AAA TTG CGT CAA CAA ATT ATC AGC ATA CAA AAC TCC AAC AGG CAA TTG ATG GGT
145  Lys Leu Arg Gln Gln Ile Ile Ser Ile Gln Asn Ser Asn Arg Gln Leu Met Gly

487  GAG ACG ATA GGG TCA ATG TCT CCC AAA GAG CTC TTA AAC TTG GAA GGC AGA TTA
163  Glu Thr Ile Gly Ser Met Ser Pro Lys Glu Leu Leu Asn Leu Glu Gly Arg Leu

541  GAG AGA AGT ATT ACC CGA ATC CGA ATC AGG AAG AAT GAG CTC TTA TTT TCT GAA
181  Glu Arg Ser Ile Thr Arg Ile Arg Ser Lys Asn Glu Leu Leu Phe Ser Glu

594  ATC GAC TAC ATG CAG AAA AGA GAA GTT GAT TTG CAT AAC GAT AAC CAG ATT CTT
199  Ile Asp Tyr Met Gln Lys Arg Glu Val Asp Leu His Asn Asp Asn Gln Ile Leu

649  CGT GCA AAG ATA GCT GAA AAT GAG AGG AAC AAT CCG AGT ATA AGT CTA ATG CCA
217  Arg Ala Lys Ile Ala Glu Asn Glu Arg Asn Asn Pro Ser Ile Ser Leu Met Pro

703  GGA GGA TCT AAC TAC GAG CAG CTT ATG CCA CCT CAA ACG CAA TCT CAA CCG
235  Gly Gly Ser Asn Tyr Glu Gln Leu Met Pro Pro Pro Gln Thr Gln Ser Gln Pro

757  TTT GAT TCA CGG AAT TAT TTC CAA GTC GCG GCA TTG CAA CCT AAC CAC CAT
253  Phe Asp Ser Arg Asn Tyr Phe Gln Val Ala Ala Leu Gln Pro Asn His His

811  TAC TCA TCC GCC GGT CGC CAA GAC CAA ACC GCT CTC CAG TTA GTG TAA
271  Tyr Ser Ser Ala Gly Arg Gln Asp Gln Thr Ala Leu Gln Leu Val *

860  TATTGGCTGAAGGAAATGGCCTGAGTGAATAAAAACCAGAATTGGGTTGAGCAAGCAATATAAAGCTAAT
931  GCATGTTATATATATATATTATCCCATGAATGTTGTATCAGTGAATTCTTATGCTTATGTTGATGTGAAATT
1002 AATATCTTAAAGACATGTCATTAATGTGCTTAATTGCTTCA
```

FIG._1C-2

```
BAG1  CAATCAACAACTTCACCCTTCCATTTCTGCAACTTCTCCAAATCTTCATACTTTCCAGAA    60
      AATCATTTCCCAAGAGAAATAAAACTTTCCTCTTTGTTCATCTCTCTTCCCCCCAACAG
      CAAAC                                                           20

BAG1  ATGGCTTACCAAATGGAGCTAGGAGGAGAATCCTCTCCACAAAGGAAAGCTGGGAGAGGA    120
   M  A  Y  Q  M  E  L  G  G  E  S  S  P  Q  R  K  A  G  R  G
AG                              D  L                                 S
                                                                     40

AAGATCGAAATAAAACGGATCGAGAACACAACGAACCGTCAAGTTACTTTCTGCAAACGC   120
   K  I  E  I  K  R  I  E  N  T  T  N  R  Q  V  T  F  C  K  R         40

AGAAAATGGTTTGCTCAAGAAAGCTTACGAACTCTCTGTTCTTTGTGATGCTGAAGTCGCA   180
   R  N  G  L  L  K  K  A  Y  E  L  S  V  L  C  D  A  E  V  A         60

CTCATTGTCTTCTCTAGCCGTGGCCGTCTCTATGAGTACTCAAACAACAGTGTAAAAGGG    240
   L  I  V  F  S  S  R  G  R  L  Y  E  Y  S  N  N  S  V  K  G         80

ACAATTGAGAGGTACAAGAAAGCAATATCGGATAATTCTAACACCGGATCCGTGGCAGAA   300
   T  I  E  R  Y  K  K  A  I  S  D  N  S  N  T  G  S  V  A  E        100

ATTAATGCACAGTATTATCAACAAGAATCTGCCAAATTGCGTCAACAAATTATCAGCATA   360
   I  N  A  Q  Y  Y  Q  Q  E  S  A  K  L  R  Q  Q  I  I  S  I        120

CAGAACTCGAACAGGCAATTGATGGGTGAGACGATTGGGTCAATGTCTCCCAAAGAGCTC   420
   Q  N  S  N  R  Q  L  M  G  E  T  I  G  S  M  S  P  K  E  L        140

AGGAACTTGGAAGGCAGATTAGACAGAAGTGTTAATCGAATCCGATCCAAGAAGAACGAA   480
   R  N  L  E  G  R  L  D  R  S  V  N  R  I  R  S  K  K  N  E        160
                              E              I  T
```

FIG._2A

```
CTCTTATTCGCCGAAATTGACTACATGCAGAAGAGAGAAGTTGATTTGCATAACGATAAC    540
 L  L  F  A  E  I  D  Y  M  Q  K  R  E  V  D  L  H  N  D  N    180
                         S
CAGCTTCTTCGTGCTAAGATAGCTGAAAATGAGAGGAACAATCCAAGTATGAGTCTGATG    600
 Q  L  L  R  A  K  I  A  E  N  E  R  N  N  P  S  M  S  L  M    200
               I                                          I
CCAGGAGGATCTAACTACGAGCAGATCATGCCACCTCCACAAACGCAACCTCAACCGTTT    660
 P  G  G  S  N  Y  E  Q  I  M  P  P  P  Q  T  Q  P  Q  P  F    220
                               L                            S
GACTCACGAAACTATTTTCAAGTCGCGGCATTGCAACCTAACAATCACCATTACTCATCC    720
 D  S  R  N  Y  F  Q  V  A  A  L  Q  P  N  N  H  H  Y  S  S    240
GCAGGTCGCGAAGACCAAACCGCTCTTCAGTTAGTGTAA                         756
 A  G  R  E  D  Q  T  A  L  Q  L  V  *                          252
                     Q
TATTGGCTGAAGCATGAAGGAGCAAGGACTGAATAAAAAACCAGAACTGGGTTAAGGAACG   816
AGCGGATATAAAGCTGATGCACTGTTATAAAATATTTATATATTTATTTCACGAATGTTG    876
TGTCCATGCTTTCTACATTTTATTATTTAAATTGCTTATGTTGATGTGAAATTAATATCTTAA 936
AAGACATGTGATTAATGTGCTTAATTTGTTTCG                               969
```

*FIG._2B*

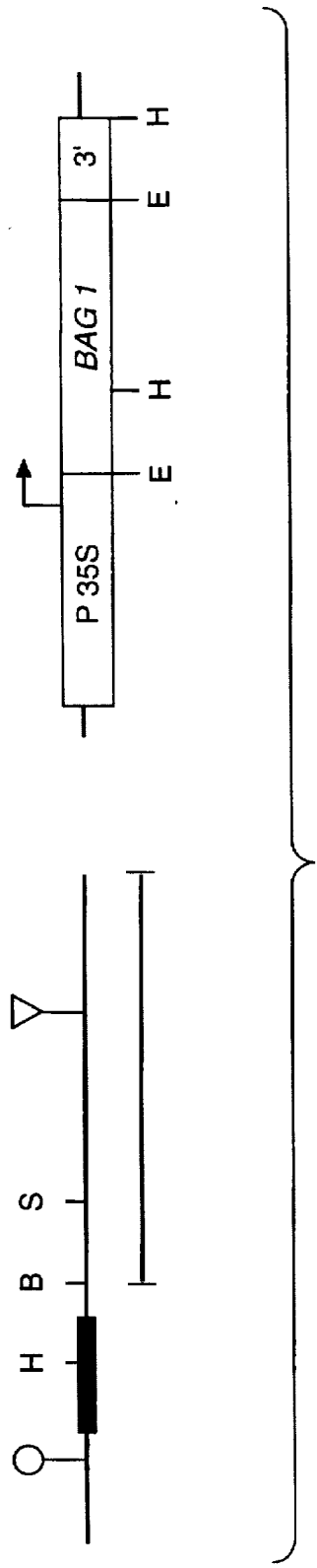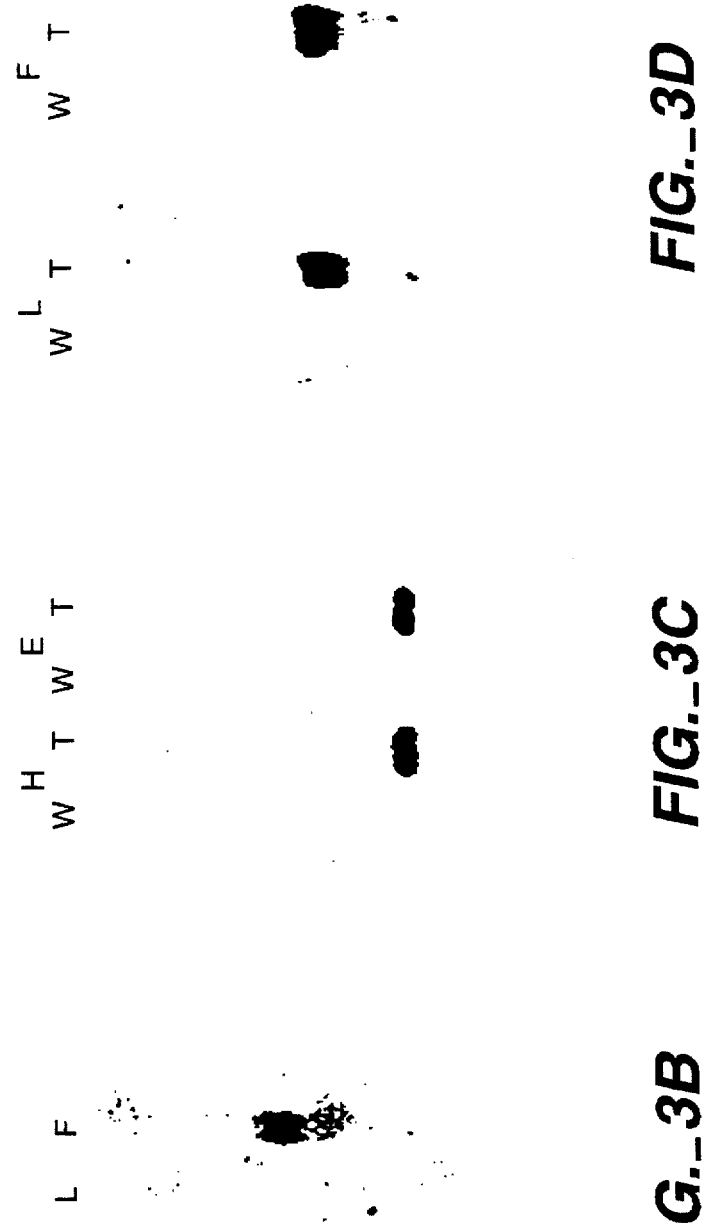
FIG._3A
FIG._3B  FIG._3C  FIG._3D

FIG._4A
FIG._4B
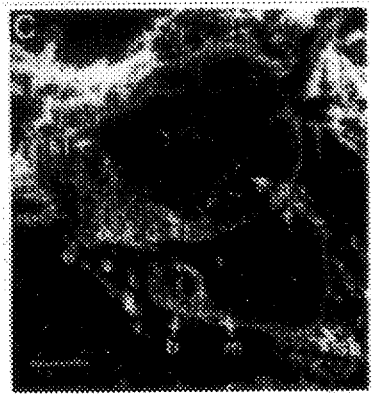
FIG._4C
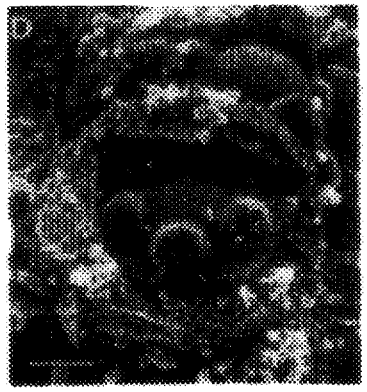
FIG._4D
FIG._4E
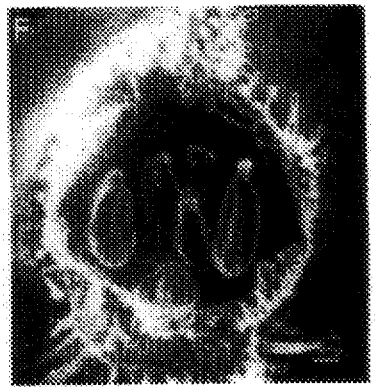
FIG._4F
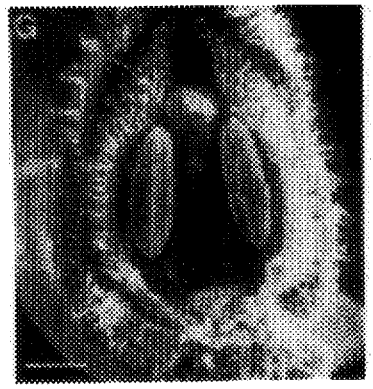
FIG._4G
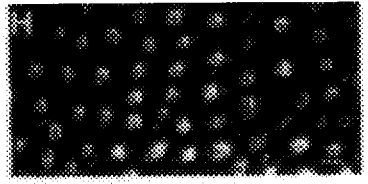
FIG._4H
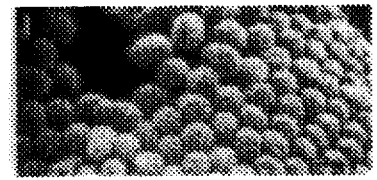
FIG._4I

FIG._5A
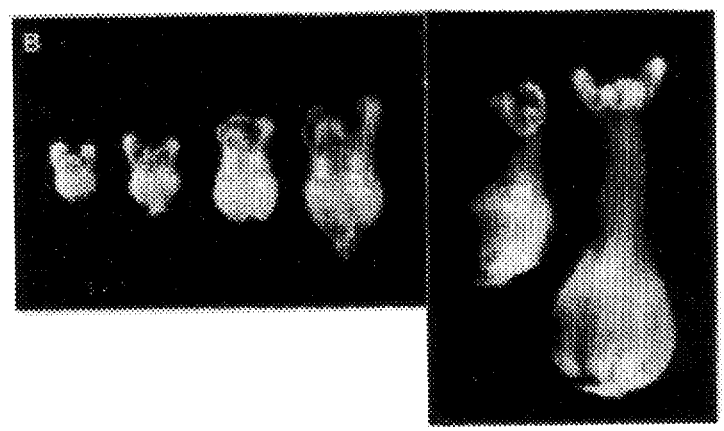
FIG._5B
FIG._5C
FIG._5D
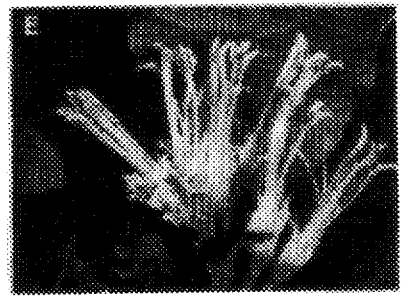
FIG._5E

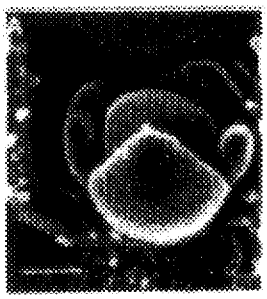
FIG._6A
FIG._6B
FIG._6C
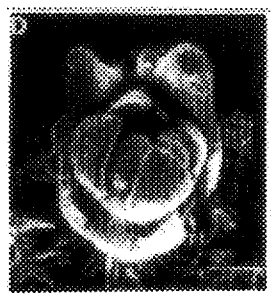
FIG._6D
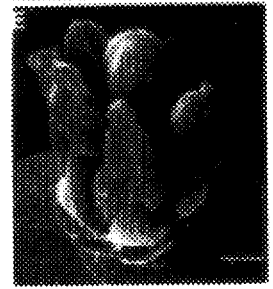
FIG._6E
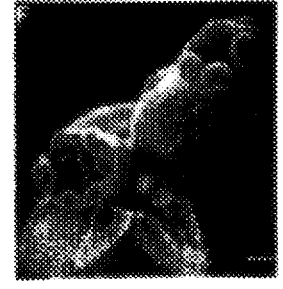
FIG._6F
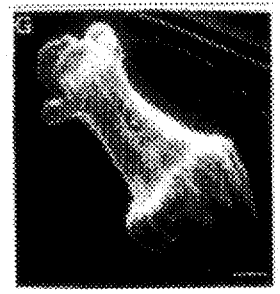
FIG._6G
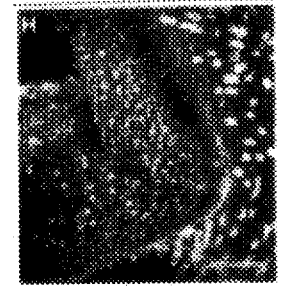
FIG._6H
FIG._6I
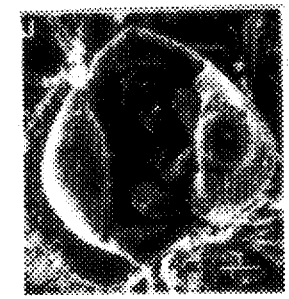
FIG._6J
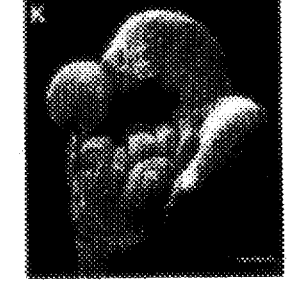
FIG._6K
FIG._6L

FIG._7A
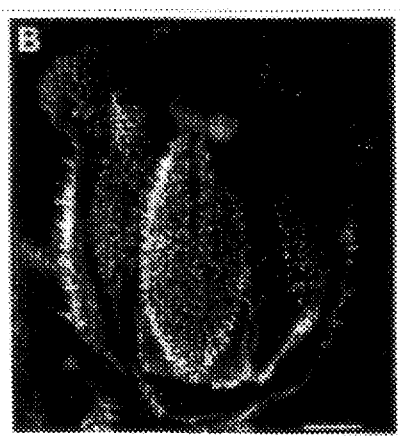
FIG._7B
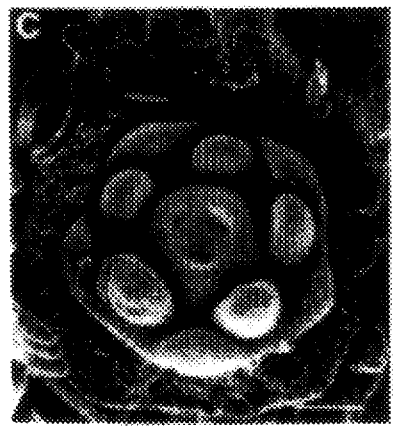
FIG._7C
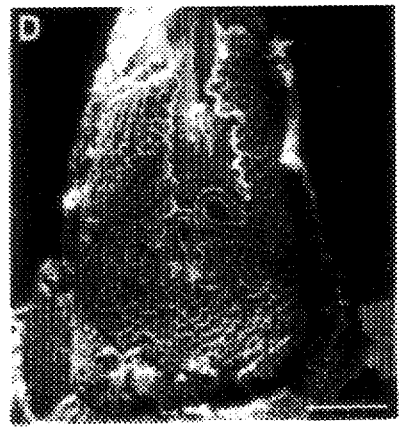
FIG._7D
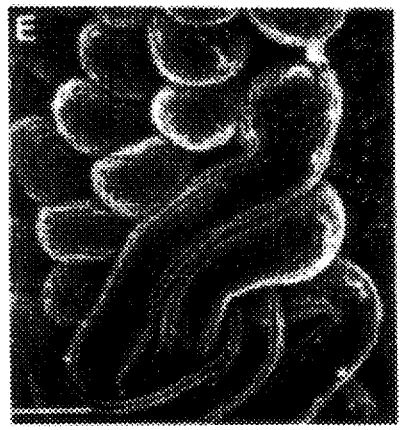
FIG._7E

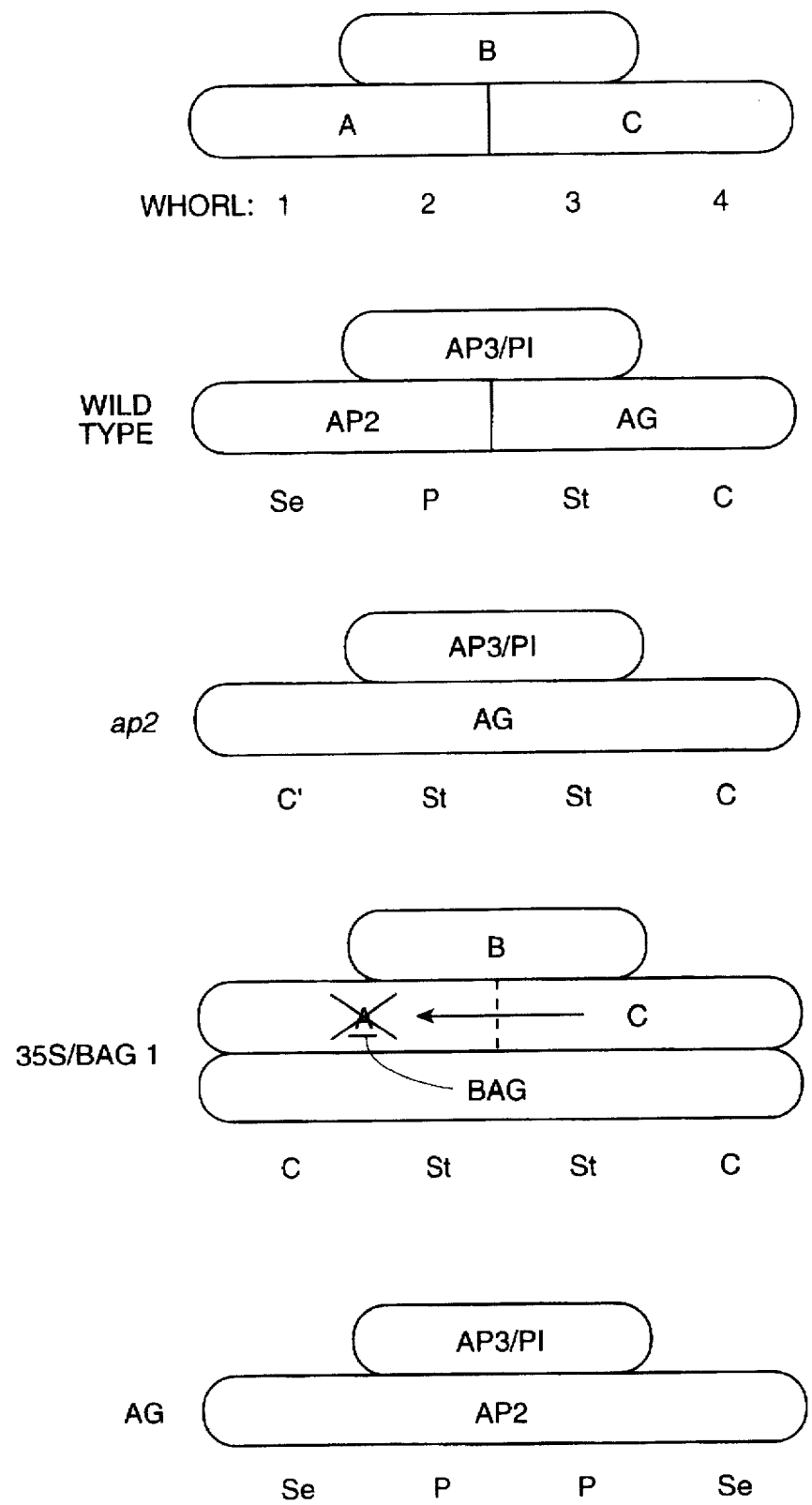
FIG._8

WHORL: 1 2 3 4
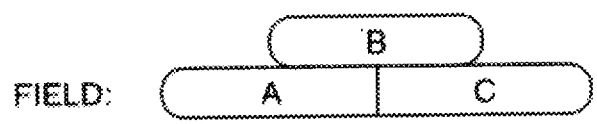
FIELD:
WILD
TYPE
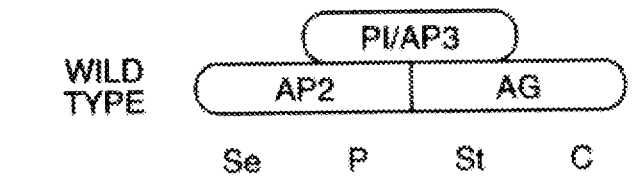 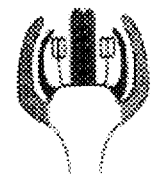
Se P St C
ap3 OR pi
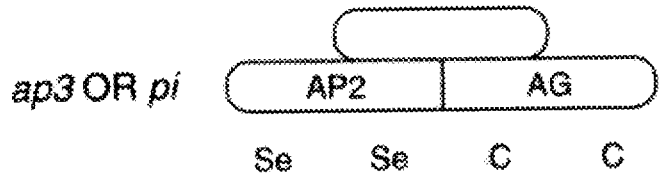 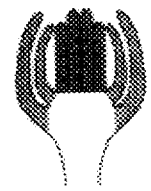
Se Se C C
ap2
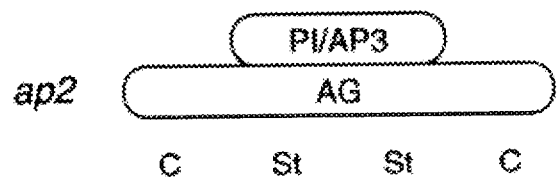 
C St St C
ag
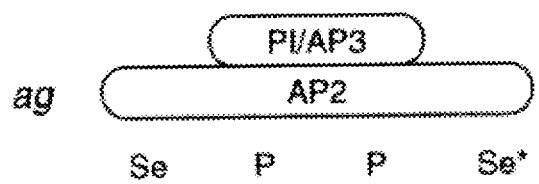 
Se P P Se*
*FIG._9A*

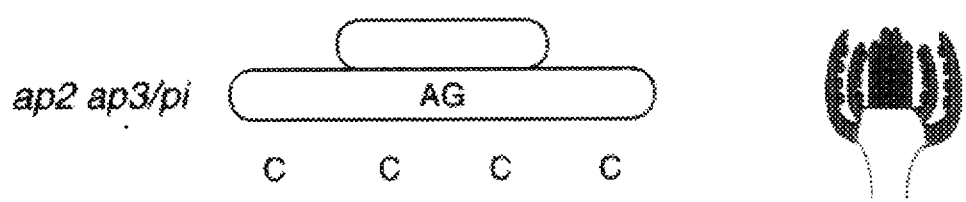
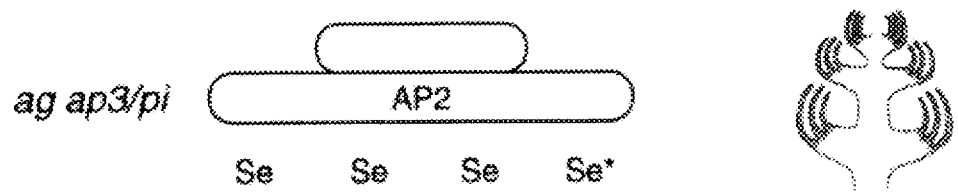
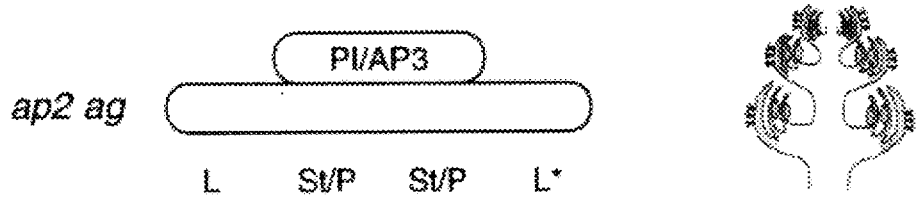
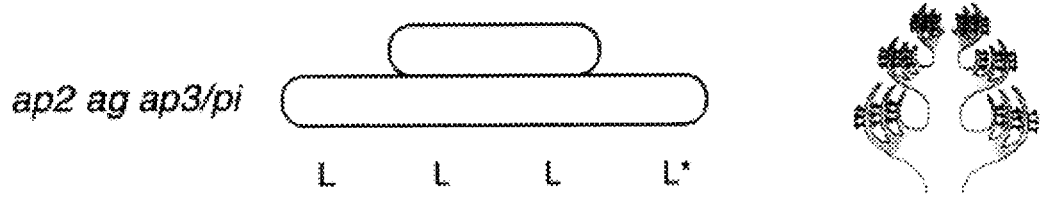
FIG._9B

FIG._10

```
GAATTCCATA TATCTATCCT CTGCAGATTA ATTTGCAAGG AAGAACTAAA AACTTTCTGT    60

ACTCTCTATT TTCATCTTCC AACCCTTTCT TTCCTTACCA GGTGAAAGT ATG GAC       115
                                                     Met Asp
                                                      1

TTC CAA AGT GAT CTA ACA AGA GAG ATC TCT CCA CAA AGG AAA CTG GGA    163
Phe Gln Ser Asp Leu Thr Arg Glu Ile Ser Pro Gln Arg Lys Leu Gly
          5                  10                  15

AGA GGA AAG ATT GAG ATC AAA CGG ATC GAA AAC ACA ACG AAT CGT CAA    211
Arg Gly Lys Ile Glu Ile Lys Arg Ile Glu Asn Thr Thr Asn Arg Gln
     20                  25                  30

GTC ACT TTC TGC AAG AGA CGC AAT GGT TTA CTC AAA AAG GCC TAT GAA    259
Val Thr Phe Cys Lys Arg Arg Asn Gly Leu Leu Lys Lys Ala Tyr Glu
 35                  40                  45                  50

TTA TCT GTG CTC TGT GAT GCT GAG GTT GCT TTG ATT GTC TTC TCA AGC    307
Leu Ser Val Leu Cys Asp Ala Glu Val Ala Leu Ile Val Phe Ser Ser
             55                  60                  65

AGA GGC AGA CTC TAT GAG TAT TAT GCC AAC AAC AGT GTG AAA GCA ACA ATT  355
Arg Gly Arg Leu Tyr Glu Tyr Tyr Ala Asn Asn Ser Val Lys Ala Thr Ile
         70                  75                  80
```

FIG._11A

```
GAG AGG TAC AAG AAA GCT TGT TCA GAT TCC TCA AAC ACT GGT TCA ATT   403
Glu Arg Tyr Lys Lys Ala Cys Ser Asp Ser Ser Asn Thr Gly Ser Ile
             85                   90                   95

TCC GAG GCC AAT GCT CAG TAT TAT CAG CAA GAA GCC TCC AAA CTG CGC   451
Ser Glu Ala Asn Ala Gln Tyr Tyr Gln Gln Glu Ala Ser Lys Leu Arg
            100                  105                  110

GCA CAA ATT GGA AAT CTG CAG AAT CAG AAC AGG AAC ATG TTG GGT GAA   499
Ala Gln Ile Gly Asn Leu Gln Asn Gln Asn Arg Asn Met Leu Gly Glu
            115                  120                  125                  130

TCA CTG GCT GCA CTG AGC CTC AGA GAT CTG AAG AAT CTG GAA CAA AAA   547
Ser Leu Ala Ala Leu Ser Leu Arg Asp Leu Lys Asn Leu Glu Gln Lys
            135                  140                  145

ATT GAA AAA GGC ATT GAG AAA ATC AGA AGC AAA AAG AAT GAG CTG CTG   595
Ile Glu Lys Gly Ile Glu Lys Ile Arg Ser Lys Lys Asn Glu Leu Leu
            150                  155                  160

TTT GCT GAA ATT GAG TAC ATG CAG AAG AGG GAA ATT GAT TTA CAC AAC   643
Phe Ala Glu Ile Glu Tyr Met Gln Lys Arg Glu Ile Asp Leu His Asn
            165                  170                  175

AAC AAT CAG TAC CTG AGA GCA AAG ATT GCT GAA ACT GAG AGA GCT CAG   691
Asn Asn Gln Tyr Leu Arg Ala Lys Ile Ala Glu Thr Glu Arg Ala Gln
            180                  185                  190
```

*FIG.—11B*

```
CAG CAG CAG CAG CAG CAG ATG AAC TTG ATG CCA GGG AGT TCA AGC                 739
Gln Gln Gln Gln Gln Gln Met Asn Leu Met Pro Gly Ser Ser Ser
195                         200                         205         210

TAT GAG CTT GTG CCT CCA CCT CAT CAA TTT GAT ACT CGA AAC TAT TTA             787
Tyr Glu Leu Val Pro Pro Pro His Gln Phe Asp Thr Arg Asn Tyr Leu
            215                         220                         225

CAA GTT AAT GGT TTG CAA ACC AAC CAT TAC ACT AGA CAA GAC CAA                 835
Gln Val Asn Gly Leu Gln Thr Asn His Tyr Thr Arg Gln Asp Gln
        230                         235                         240

CCA TCT CTT CAA CTA GTC TAATATGGTT GAAAGTCTTC TATGTTTTGT                    883
Pro Ser Leu Gln Leu Val
            245

GCTCTACATC TTAACCACAA GAGAAGACTA CTATTAAGCC TGAAGATTCT TGGAAGTGAA           943

GATCAACTTA ATTATGTATA CCATATTATA TTACTTGCTG AATGAGCTGA GACTCTTCAA          1003

TGTTGTATGT TAAGTGGATA TGTATTTTTT AGTTGATGTT CCTTGTCTGG CAGTGTACTA          1063

TGAGGAATTA CGCTTGTTAT TATTAAGTTG ACAACTACTG TTTATTTGC TCAAAAAAAA           1123

PLANTS HAVING ALTERED FLORAL DEVELOPMENT

This is a continuation of application Ser. No. 08/293,278, filed Aug. 19, 1994, now abandoned, which is a continuation of application Ser. No. 07/956,694, filed Oct. 2, 1992, now abandoned.

The U.S. Government has certain rights in this invention pursuant to Contract No. DCR 8303439, awarded by the National Science Foundation.

TECHNICAL FIELD OF THE INVENTION

The invention relates to the use of recombinant nucleic acids derived from an agamous gene to produce plants having a phenotype characterized by altered floral development.

BACKGROUND OF THE INVENTION

Naturally occurring variations in floral development in plants have been recognized for centuries. Manmade induced mutations such as by random mutation utilizing chemical mutagenesis by ethylmethane sulphonate or T-DNA insertion mutation have also resulted in modification of floral phenotype. See, e.g., Koornneef, et al. *Arabidopsis Inf. Serv.* 17:11–18 (1980) and Feldmann, et al. *Science* 243:1351–1354 (1989).

*Arabidopsis thaliana* has been widely used for molecular and genetic studies of developmental processes in plants (Meyerowitz, et al. *Ann. Rev. Genet.* 21:93–111 (1987); Meyerowitz *Cell* 56:263–269 (1989)). Many mutations affecting floral morphogenesis have been identified in Arabidopsis. Mutations in at least four genes result in homeotic transformation of floral organs (Meyerowitz (1987), supra.; Bowman, et al. *The Plant Cell* 1:37–52 (1989); Koornneef, M. in *Genetic Maps* (1987) 742–745 (Cold Spring Harbor Laboratory, New York); Pruitt, et al. in 45th Symposium of the Society for Developmental Biology (Loomis, W., eds.) 327–338 (Liss, New York, 1987); Komaki, M. K., et al. *Development* 104:195–203 (1988), and Kunst, et al. *The Plant Cell* 1:1131–1135 (1989)). In general, these homeotic mutations affect the development of adjacent whorls of floral organs. For example, the ap2-1 mutation in the apetala2 gene (AP2) results in the conversion of the sepals into leaf-like organs and in the conversion of petals into stamen-like organs. Mutations in the apetala3 (AP3) (ap3-1) or pistillata (PI) (pi-2) genes results in the conversion of petals into sepals and stamens into carpels. Mutations in the agamous (AG) gene result in the overall phenotype of a flower within a flower and the absence of stamens and carpels. The homeotic gene agamous from *Arabidopsis thaliana* has been cloned (Yanofsky, et al. *Nature* 346:35–39 (1990)).

Recently, other mutations have been identified in the apetala2 (ap2-2, ap2-8 and ap2-9); pistillata (pi-3) and agamous gene (ag-2 and ag-3) and their potential interaction with each other have been described (Bowman, et al. *Development* 112:1–20 (1991)). In addition, tissue specific expression of the agamous gene (Bowman, et al. *Plant Cell* 3:749–758 (1991)) and a proposed regulatory mechanism for controlling the agamous gene by the apetala2 gene product (Drews, et al. *Cell* 85:991–1002 (1991)) have been reported.

The foregoing have contributed to the understanding of the molecular basis of flower development. However, each of the foregoing floral phenotypes is based upon either naturally occurring variants or random mutagenesis each of which have the potential to revert to the wild-type phenotype.

Accordingly, an object of the invention is to provide transformed plants containing nucleic acids derived from an agamous gene which confer a phenotype characterized by altered floral development in the plant.

Still further, it is an object herein to provide vectors and methods utilizing such vectors to transform one or more plant cells such that a plant containing one or more of such transformed cells has an altered floral phenotype.

SUMMARY

In accordance with the foregoing objects, the invention includes plants having at least one cell transformed with a vector comprising at least a portion of an agamous nucleic acid. Such plants have a phenotype characterized by altered floral development.

The invention also includes vectors capable of transforming a plant cell to alter floral development. In one embodiment the vector comprises a nucleic acid containing at least a portion of an agamous nucleic acid operably linked to a promoter other than the promoter naturally associated with the agamous nucleic acid. In an alternate embodiment, the vector comprises at least a portion of an agamous nucleic acid operably linked in an antisense orientation to a promoter.

The invention also includes methods for producing plants having altered floral development. The method comprises the steps of transforming plant cells with a vector comprising at least a portion of an agamous nucleic acid; regenerating plants from one or more of thus transformed plant cells and selecting at least one plant exhibiting altered floral development.

This file of this patent contains at least one drawing executed in color. Copies of this patent with color drawings (s) will be provided by the Patent and Trademark Office upon request and payment of the necessary fee.

BRIEF DESCRIPTION OF THE DRAWINGS

FIG. 1 depicts the restriction map, genomic structure and nucleic (SEQ ID NO:01) and amino acid (SEQ ID NO:02) sequence of the agamous gene from *Arabidopsis thaliana*. The DNA binding domain extends from amino acid residue 51 through amino acid residue 109. From Yanofsky et al., *Nature* 346, 35–39 (1990).

FIG. 2 depicts the cDNA (SEQ ID NO:03) and deduced amino acid sequence (SEQ ID NO:04) of the BAG1 gene, the AG homolog in *Brassica napus*. The amino acid residues that differ in AG (SEQ ID NO:05) from Arabidopsis are shown below the BAG1 sequence (SEQ ID NO:04). The numbers to the right indicate the position relative to the putative translation start site. The DNA binding domain extends from amino acid residue 18 through amino acid residue 76.

FIG. 3A is a schematic diagram of BAG1 cDNA and 35S/BAG1 constructs used in the examples. The upper line indicates the 1.1 kb BAG1 cDNA and the fillbox indicates the MADS box region. The line below the cDNA indicates the restriction fragment to use as probe (pKY14) for the RNA and DNA blots. The translation start and stop codons are indicated by open circle and triangle, respectively. To the right of the cDNA is a schematic representation of the construct used to generate transgenic plants. P35S denotes the 35S promoter from cauliflower mosaic virus; BAG1 denotes the BAG1 cDNA; the 3' end is from the nopaline synthase gene. Restriction sites include EcoRI (R), HindIII (H), BamHI (B) and SacI (S).

FIG. 3B demonstrates the expression of BAG1 gene and wild-type plants. Approximately 20 μm total RNA from leaves (L) and flowers (F) of *Brassica napus* was size fractionated, transferred to nylon membranes and hybridized with a probe specific to the 3' portion of the BAG1 cDNA (see FIG. 3A). The hybridizing RNA is approximately 1.1 kb in length.

FIG. 3C is a DNA blot of wild-type and 35S/BAG1 transgenic tobacco. Approximately 10 μg of DNA from wild-type (W) and 35S/BAG1 transgenic (T) plants was digested to completion with EcoRI (E) or HindIII (H), size fractionated, transferred to nylon membranes, and hybridized with a probe specific for the 3' end of the BAG1 gene (see FIG. 3A) as described in Experimental Procedures. The hybridizing DNA fragments are approximately 1.1 kbp in length.

FIG. 3D is an RNA blot of wild-type and 35S/BAG1 transgenic tobacco. Approximately 20 μg of total RNA from leaves (L) and flowers (F) of wild-type (W) and 35S/BAG1 transgenic (T) tobacco plants was size fractionated, transferred to nylon membranes, and hybridized with a probe specific for the 3' portion of the bag1 cDNA (see FIG. 3A). The hybridizing RNAs are approximately 1.1 kb in length.

FIG. 4 contains scanning electron micrographs depicting the development of wild-type *Nicotiana tobacum* var. Xanth flowers. In many cases the outer whorl organs have been dissected away to reveal the inner whorls.

FIG. 4A shows Stage 2 and 4 flowers. Three sepal primordia (se) are visible on the Stage 2 flower (only the second initiated one is labeled), the older sepal primordium being abaxial with respect to the stage 4 flower. The bract (b) and the axillary meristem (m) associated with the stage 2 flower are also visible. The stage 2 flower developed from the axillary meristem associated with the stage 4 flower, which in turn developed from the axillary meristem associated from the next oldest flower which has been removed.

FIG. 4B shows a stage 3 flower in which all five sepal primordia have formed. Note the difference in size between the first and later formed primordia.

FIG. 4C shows stage 2 and 5 flowers. The first sepal primordium (se) has emerged on the stage 2 flower. The bract (b) and associated meristem (m) of the stage 2 flower are also visible. Three sepal primordia have been removed from the stage 5 flower revealing the five small second whorl petal primordia (p) and the five third whorl stamen primordia (st).

FIG. 4D shows a stage 5 flower. The five second whorl petal primordia are alternate with the sepals and the five third whorl stamen primordia are opposite the sepals.

FIG. 4E shows that two horseshoe-shaped fourth whorl carpel primordia (c) have formed in this stage 6 flower. The second whorl petals have connately fused at their bases by this time (arrow). Note the size difference of the first whorl sepals in the stage 4 flower (f).

FIG. 4F shows that two fourth whorl carpels of this stage 7 flower are nearly fused. Filaments and anther regions are clearly evident in the third whorl stamens. The sepals have grown to enclose the interior organs by this stage.

FIG. 4G shows a mature flower in which cellular differentiation is evident in all four whorls of organs. The bases of the filaments are adnately fused to the second whorl petals. Meiosis is occurring in the anthers and stigmatic tissue is developing on the top of the style.

FIG. 4H shows an adaxial view of a mature petal limb. The epidermal cells are uniformly sized and characterized by cuticular thickenings.

FIG. 4I shows ovules arising from the central placental tissue of the ovary. Bars=100 μg, except for FIG. 4 B and H where Bar is 10 μg.

FIG. 5 consists of photographs of wild-type and 35S/BAG1.1 transgenic flowers.

FIG. 5A shows a series of developing wild-type flowers.

FIG. 5B shows a series of developing 34S/BAG1.1 transgenic flowers. Length of smallest bud is 3 m; length of largest bud is 13 mm.

FIG. 5C shows the phenotypes of wild-type (left) and transgenic flowers with increasing levels of deviations from wild-type.

FIG. 5D shows inflorescence from wild-type plant.

FIG. 5E shows inflorescence from a transgenic plant with an intermediate phenotype.

FIG. 6 consists of scanning electron micrographs depicting the development of transgenic tobacco flowers from line 35S/BAG1.1. In many cases, the outer whorl organs have been dissected away to reveal the inner whorls.

FIG. 6A is a stage 3 flower. Only four distinct first whorl primordia are evident, each of which will develop into a carpelloid organ.

FIG. 6B is a stage 5 flower. Positions and numbers of outer three whorls of organ primordia are similar to that of wild-type.

FIG. 6C is a stage 6 flower. Five-second whorl and five third whorl organ primordia are present in their normal positions.

FIG. 6D shows a flower where the second whorl organs (2) are petalloid stamens, while the first whorl organs are carpelloid with some placental tissue (pt) visible at the adaxial base of the first whorl.

FIG. 6E shows that all second and third whorl organs, of which there are only seven visible, are staminoid, although most are severely deformed. The fourth whorl gyneocium also has some morphological deformities.

FIG. 6F is an overview of inflorescence. The outer whorl organs, which develop as carpels, often fused completely impeding the growth of the organs of the interior whorls such that the mature flowers resemble a single five-carpelled ovary.

FIG. 6G is an overview of a single relatively mature flower. The overall structure closely resembles that of an ovary, with a broad region a the base in which placental tissue bearing ovule-like structures develops, a long region resembling a style, which is capped with stigmatic papillae. The epidermal cells of the first whorl organs resembles that of carpels, and an orange ring of tissue from which nectar is secreted is evident at the base of the first whorl organs.

FIG. 6I is a relatively mature flower in which the outer portions, the ovary walls, of the first whorl organs have been removed revealing the placental tissue (pt) from which ovule-like (o) structures develop. The second and third whorl organs are staminoid and deformed.

FIG. 6J is a transgenic flower that exhibits a severely abnormal phenotype. All the organs primordia appear fused at this point, and it is difficult to trace their origins to specific whorls. All the organ primordia will most likely develop into carpelloid structures.

FIG. 6K is a transgenic flower in which organs of all whorls are carpelloid as evidenced by the stigmatic papillae on the organs. All organs are fused together into a single structure precluding further dissection.

FIG. 6L shows an anther of a third whorl organ displaying abnormal growth. Bars=100 μm.

5

FIG. 7 consists of scanning electron micrographs depicting transgenic tobacco flowers from line 35SBAG1.2 and depicting the ovules arising from the fourth whorl.

FIG. 7A shows that the first whorl organs are carpelloid sepals. They are fused to a greater extent than wild-type sepals and are curled at their tips. Stigmatic papillae are visible at the apices of their margins of fusion. The second whorl organs are staminoid petals; the apices that in wild-type would expand into the large limb of the petal, remain small and curled inward.

FIG. 7B shows that the second whorl staminoid petals do not fuse like wild-type second whorl petals. They also do not fuse adnately to the third whorl organs.

FIG. 7C is a stage 6 flower in which three instead of two fourth whorl organ primordia have formed. Bars=100 µm.

FIG. 7D shows a central ovary of a 35S/BAG1.2 flower in which several elongated structures have developed in positions normally occupied by ovules. The abnormal structures develop primarily at the margins of the placenta. The outer wall of the ovary has been dissected away.

FIG. 7E is a close up of FIG. 7D. Tissue resembling stigmatic papillae is evident at the tips of the elongate structures. Apparently morphologically normal ovules (top left, see FIG. 4I) develop in positions adjacent to the abnormal structures. Bar=100 µm.

FIG. 8 depicts a model demonstrating how three classes of homeotic genes can specify organ identity for each of four whorls in a floral organ.

FIG. 9 depicts the various combinations of phenotypes which can be obtained by combining the and/or AP2 phenotype with AP3 and/or PI phenotypes. The phenotype is identified at the left with the distribution of gene products indicated by uppercase letters within the boxes. The detailed phenotype of the organs in each whorl are shown under the diagrams where SE=sepal, P=petal ST=stamen, C=carpel, P/ST=petelloid stamen (an organ characteristic of both petals and stamens) and L=leaf or carpelloid leaf. When the AG phenotype is present, the asterisk indicates that there are several whorls of organs interior to the fourth whorl. A schematic drawing of a longitudinal cross-section of each phenotype of flower is depicted to the right. Each of the organ types is color coded: sepals=green, petals=pink, stamens=yellow, carpel=orange, petelloid stamens=gold and leaves and carpelloid leaves=blue. The whorls interior to whorl 9 in the AG containing phenotypes are not shown.

FIG. 10 is a color photograph of a flower from Nicotiana exhibiting the AG phenotype of a flower within a flower.

FIG. 11 depicts the cDNA (SEQ ID NO:06) and amino acid (SEQ ID NO:07) sequence of the agamous gene (NAG1) from *Nicotiana tabacum*. The DNA binding domain extends from amino acid residues 17 through amino acid residue 75.

DETAILED DESCRIPTION OF THE INVENTION

The invention provides plants having cells transformed with a vector comprising at least a portion of an organic gene. Such plants have a phenotype characterized by altered floral development. The members of the Kingdom Plantae which can be used to practice the invention include plants within the Division Magnoliophyta, i.e., the angiosperms include dicotyledons (Class Magnoliopsida and Dicotyledoneae) and monocotyledons (Class Liliosida). The angiosperms comprise plants having seeds enclosed in an ovary and are generally characterized as being flowering

6 plants. Particularly preferred Orders of angiosperm according to "Taxony of Flowering Plants", by A. M. Johnson, The Century Co., NY 1931 include Rosales, Cucurbitales, Rubiales, Campanulatae, Contortae, Tubiflorae, Plantaginales, Ericales, Primulales, Ebenales, Diapensiales, Primulales, Plumbaginales, Opuntiales, Parietales, Myritiflorae, Umbelliflorae, Geraniales, Sapindales, Rhamnales, Malvales, Pandales, Rhoendales, Sarraceniales, Ramales, Centrospermae, Santalales, Aristolochiales, Julianiales, Juglandales, Fagales, Urticales, Myricales, Polygonales, Batidales, Balanopsidales, Proteales, Salicales, Leitneriales, Garryales, Verticillatae and Piperales. Particularly preferred plants include lily, carnation, chrysanthemum, petunia, rose, geranium, violet, gladioli, orchid, lilac, crabapple, sweetgum, maple, locust, ash and linden tree.

Gymnosperms can also be used to practice the invention. Gymnosperms are classified within the Division Pinophyta. Especially useful gymnosperms are those within the class Pinopsida, and in particular the order Pinales. Although gymnosperms have seeds which are exposed and not enclosed in an ovary, such plants have structures which are analogous to that found in the angiosperms and thus can be modified in a manner analogous to angiosperms to alter the development of the corresponding reproductive tissue. For example, members of the genus Pinus can be modified to produce a phenotype characterized by altered floral development wherein the pollen producing capability of the male sex organ is modified to produce a male sterile plant.

It is to be understood that the parent plant used to practice the invention can be a wild-type variant or a variant which has been modified by human intervention by either random mutagenesis, e.g., chemical or x-ray mutation or by other modifications utilizing recombinant techniques either to modify endogenous loci or to introduce exogenous DNA to modify the genotype of the parent plant. In general, the plants used to practice the invention contain an endogenous agamous. Such plants can be readily identified by analyzing genomic DNA for the presence of nucleic acid sequences comprising an agamous gene as defined hereinafter.

As used herein, the term "altered floral development" or "modified floral phenotype" refers to a physical modification in the structure of a plant's reproductive tissue as compared to the parent plant from which the plant having the modified phenotype is obtained. Such modified floral phenotypes can be uniform throughout the plant and typically arise when each of the cells within the plant contain cells transformed with a vector comprising at least a portion of an agamous nucleic acid. Such plants are sometimes referred to as transgenic plants. Alternatively, the altered phenotype can comprise a mixed phenotype wherein only a subset of the reproductive tissue has been modified in physical characteristic as compared to the parent plant. Such phenotypes can be obtained by producing a mosaic plant containing cells derived from the parent plant and cells transformed with the vector of the invention. Alternatively, the vector used to make a transgenic or mosaic plant containing an inducible promoter such as one from a heat-shock protein gene. Localized exposure of a portion of the plant to appropriate temperature to activate such a promoter induces the altered phenotype in the portion of the plant so treated and in those tissues containing the inducible promoter.

The phenotype produced in a particular plant is dependent upon the design of the vector used to produce it. Thus, the vector can be designed to transcribe a nucleic acid which encodes at least a portion of an agamous protein. In such cases, the agamous protein so produced is capable of conferring a particular phenotype based on the presence of that protein within the cell. Alternatively, the vector can be constructed such that transcription results in the formation of a transcript which is capable of hybridizing with an RNA transcript of an endogenous agamous gene. This approach employs the well known antisense technology and results in a modulation in the phenotypic effect of the endogenous agamous genes. Such modulation of the endogenous agamous genes can also potentially be obtained by using the sense strand of the agamous gene to cause sense suppression of the endogenous agamous alleles as well as the transformed agamous gene. The production of a plant containing such a phenotype is contemplated based upon the sense suppression observed in *Petunia hybrida* as set forth in PCT Publication W090/12084. The term agamous nucleic acid is sometimes used to refer to the sense and antisense strands of an agamous gene collectively.

As used herein, an "agamous gene" refers to genomic DNA or other nucleic acid which encodes an agamous protein. A genomic agamous gene includes the promoter and other expression regulation sequences as well as initiation and termination sequences for transcription and translation. The cDNA (SEQ ID NO:01) and amino acid (SEQ ID NO:02) sequence for the agamous gene from *Arabidopsis thaliana* is shown in FIG. 1 together with a restriction map and a diagram showing the location of exons and introns of the agamous gene. The agamous cDNA sequence (SEQ ID NO:03) from *Brassica napus* together with the deduced amino acid sequence (SEQ ID NO:04) of the BAG1 gene is shown in FIG. 2. The amino acid residues which differ in the agamous gene (SEQ ID NO:05) from *Arabidopsis thaliana* are shown below the BAG1 sequence (SEQ ID NO:04). The cDNA (SEQ ID NO:06) and amino acid (SEQ ID NO:07) for the agamous gene from *Nicotiana tabacum* is shown in FIG. 11.

The agamous gene product is believed to encode a transcription factor based on sequence similarity within the amino terminal portion of the agamous protein to transcription factors from human and yeast. This sequence is known to bind nucleic acids and is highly conserved among such transcription factors. Thus, the agamous protein can be divided into at least two domains. The first domain is a DNA binding domain (MADS box) comprising sequences within the amino terminal portion of the molecule. The second domain comprises the remaining sequence portion(s). Accordingly, an agamous gene is characterized by DNA and/or amino acid sequence homology to the sequences shown in FIGS. 1, 2 and 11. In this regard, it should be noted that the homology within the DNA binding domain in general is about 90 to 95% and in many instances such sequences are 100% homologous. However, in the sequence portion not consisting of the DNA binding domain the homology between agamous genes can be as low as 50% but can be as high as 75% or greater. The overall homology of the protein (SEQ ID NUMBERS:02,04,05) is preferably greater than 60%, more preferably greater than 75% and most preferably greater than 90%. However, it is to be understood that the term agamous gene or agamous protein also includes allelic variations found in nature and manmade modifications including the substitution, deletion and/or insertion of one or more nucleotides or amino acid residues in the agamous nucleic acid or agamous protein.

The vectors used to transform plant cells comprise an agamous nucleic acid or portion thereof which is capable of hybridizing with an agamous gene. Thus, such nucleic acids include the positive strand of an agamous gene encoding all or part of an protein and the antisense strand. In either case, the agamous nucleic acid or its transcript is capable of hybridizing with an agamous gene as defined herein or its transcript. The conditions under which such hybridization occurs include the physiological or equivalent conditions found within plant cells including that found in the nucleus and cytoplasm as well as standard in vitro conditions normally used by the skilled artisan to determine sequence homology as between two nucleic acids. Such in vitro conditions range from moderate (about 5×SSC at 52° C.) to high (about 0.1×SSC at 65° C.) stringency conditions.

In the preferred embodiments, an agamous nucleic acid from Arabidopsis (SEQ ID NO:01) Brassica (SEQ ID NO:03) and Nicotiana (SEQ ID NO:06) are used to confer a modified floral phenotype. However, the invention is not limited to these particular agamous nucleic acids and the particular plants having such modified phenotype. Rather, agamous genes from other sources can be used as a source of nucleic acid to practice the invention in plants containing endogenous agamous gene. The cloning of such other agamous genes and the identification of plants containing such genes can be readily obtained utilizing probes encoding all or part of that portion of the agamous proteins as set forth in FIGS. 1, 2 and 11 (SEQ ID NUMBERS:02, 04, 05) which do not encode the DNA binding domain or which contain sufficient overall sequence such that the probe preferentially binds to an agamous gene. However, because of the redundancy in the genetic code, the nucleic acid sequence homology as between those sequences (SEQ ID NUMBERS:01, 03, 06) in FIGS. 1, 2 and 11 and a putative agamous gene in another plant species may be substantially less than the above homology for amino acid sequence. Thus, genomic clones from a particular plant species can be assayed with the above described probes initially under the above relatively moderate stringency conditions. Positive clones can then be sequenced and the deduced amino acid sequence compared to that set forth in FIGS. 1 (SEQ ID NO:02), 2 (SEQ ID NO:04) or 11 (SEQ ID NO:07). Those clones which encode a homologous protein can then be used to practice the invention or to derive other clones from the genomic library using high stringency hybridization conditions. Further, those plants containing an endogenous agamous gene can be used as a parent to generate a modified floral phenotype.

Once an agamous gene has been cloned and identified, it is used to construct sense or antisense vectors for transforming plant cells. The construction of such vectors is facilitated by the use of a shuttle vector which is capable of manipulation and selection in both plant and a convenient cloning host such as a prokaryote. Thus, such a shuttle vector can include a kanamycin resistance gene for selection in plant cells and in actinomycin resistance gene for selection in a bacterial host. Such shuttle vectors, of course, also contain an origin of replication appropriate for the prokaryotic host used and preferably at least one unique restriction site or a polylinker containing unique restriction sites to facilitate vector construction. An example of such a shuttle vector is pMON530.

In the preferred embodiments, which comprise the best mode for practicing the invention, a constitutive promoter is used to drive expression of an agamous nucleic acid within at least a portion of the reproductive tissues in the recipient plant. A particularly preferred promoter is the cauliflower mosaic virus 35S protein promoter (Guilley et al. *Cell* 30:763–773 (1982); Odell, et al. *Nature* 313:810–812 (1985); and Sanders, et al. *Nucl. Acids Res.* 15:1543–1558 (1987)). However, other constitutive promoters can be used such as the $\alpha$-1 and $\beta$-1 tubulin promoter (Silflow, et al.

*Devel. Genet.* 8:435–460 (1987)); and the histone promoters (Chaubet, et al. *Devel. Genet.* 8:461–473 (1987)).

In some embodiments, an inducible promoter can be used. Examples of such promoters include those from heat-shock protein genes such as the PHS1 heat-shock protein gene (Takahashi, et al. *Mol. Gen. Genet.* 219:365–372 (1989)) and light-inducible promoters including the three chlorophyll a/b light harvesting protein promoters (Leutwiler, et al. *Nucl. Acids Res.* 14:4051–4064 (1986)) and the preferredoxin promoter (Vorst, et al. *Plant Mol. Biol.* 14:491–499 (1990)). Other promoters which can be used include the promoters for the agamous gene, the apetala2 gene, the apetala3 gene and the pistillata gene. Since these latter genes are associated with differentiation of reproductive tissue, such promoters are expected to provide tissue and temporal specificity to the expression of the agamous nucleic acid.

In addition to the foregoing promoters, pollen-specific promoters can be used. Such promoters are well-known in the art and are readily available. An example of such a promoter is Zn13 (Hamilton et al., (1992) *Plant Molecular Biology*, Vol. 18, 211–218). This promoter was cloned from corn (a monocot) but functions as a strong and pollen-specific promoter when used in tobacco (a dicot). When such a pollen-specific promoter is used to express the agamous protein, the floral phenotype comprises male sterility.

In a further embodiment of the invention, the vector used to transform the plant cell to produce a plant having an altered floral phenotype is constructed to target the insertion of the agamous nucleic acid into an endogenous promoter within a plant cell. One type of vector which can be used to target the integration of an agamous nucleic acid to an endogenous promoter comprises a positive-negative selection vector analogous to that set forth by Monsour, et al. *Nature* 336:348–352 (1988) which describes the targeting of exogenous DNA to a predetermined endogenous locus in mammalian ES cells. Similar constructs utilizing positive and negative selection markers functional in plant cells can be readily designed based upon the identification of the endogenous plant promoter and the sequence surrounding it. When such an approach is used, it is preferred that a replacement-type vector be used to minimize the likelihood of reversion to the wild-type phenotype.

The vectors of the invention are designed such that the promoter sequence contained in the vector or the promoter sequence targeted in the plant cell genome are operably linked to the nucleic acid encoding the agamous gene. When the positive strand of the agamous gene is used to express all or part of the agamous protein, the term "operably linked" means that the promoter sequence is positioned relative to the coding sequence of the agamous nucleic acid such that RNA polymerase is capable of initiating transcription of the agamous nucleic acid from the promoter sequence. In such embodiments it is also preferred to provide appropriate ribosome binding sites, transcription initiation and termination sequences, translation initiation and termination sequences and polyadenylation sequences to produce a functional RNA transcript which can be translated into agamous protein. When an antisense orientation of the agamous nucleic acid is used, all that is required is that the promoter be operably linked to transcribe the agamous antisense strand. Thus, in such embodiments, only transcription start and termination sequences are needed to provide an RNA transcript capable of hybridizing with the mRNA or other RNA transcript from the endogenous agamous gene. In addition to promoters, other expression regulation sequences, such as enhanxers, can be added to the vector to facilitate the expression of agamous nucleic acid in vivo.

Once a vector is constructed, the transformation of plants can be carried out in accordance with the invention by essentially any of the various transformation methods known to those skilled in the art of plant molecular biology. Such methods are generally described in *Methods and Enzymology*, Vol. 153 ("Recombinant DNA Part D") 1987, Wu and Grossman. Academic Press, eds. As used herein, the term "transformation" means the alteration of the genotype of a plant cell by the introduction of a nucleic acid sequence. Particular methods for transformation of plant cells include the direct microinjection of the nucleic acid into a plant cell by use of micropipettes. Alternatively, the nucleic acid can be transferred into a plant cell by using polyethylene glycol (Paszkowski et al. *EMBO J.* 3:2717–2722 (1984)). Other transformation methods include electroporation of protoplasts (Fromm, et al. *Proc. Natl. Acad. Sci. USA* 82:5824 (1985); infection with a plant specific virus, e.g., cauliflower mosaic virus (Hohn et al. "Molecular Biology of Plant Tumors", Academic Press, New York (1982), pp. 549–560) or use of transformation sequences from plant specific bacteria such as *Agrobacterium tumefaciens*, e.g., a Ti plasmid transmitted to a plant cell upon infection by *Agrobacterium tumefaciens* (Horsch et al. *Science* 233:496–498 (1984); Fraley et al. *Proc. Natl. Acad. Sci. USA* 80:4803 (1983)). Alternatively, plant cells can be transformed by introduction of nucleic acid contained within the matrix or on the surface of small beads or particles by way of high velocity ballistic penetration of the plant cell (Klein et al. *Nature* 327:70–73 (1987)).

After the vector is introduced into a plant cell, selection for successful transformance in typically carried out prior to regeneration of a plant. Such selection for transformation is not necessary, but facilitates the selection of regenerated plants having the desired phenotype by reducing wild-type background. Such selection is conveniently based upon the antibiotic resistance and/or herbicide resistance genes which may be incorporated into the transformation vector.

Practically all plants can be regenerated from cultured cells or tissues. As used herein, the term "regeneration" refers to growing a whole plant from a plant cell, a group of plant cells or a plant part. The methods for plant regeneration are well known to those skilled in the art. For example, regeneration from cultured protoplasts is described by Evans et al. "Protoplasts Isolation and Culture", *Handbook of Plant Cell Cultures* 1:124–176 (MacMillan Publishing Co., New York (1983); M. R. Davey, "Recent Developments in the Culture and Regeneration of Plant Protoplasts", *Protoplasts* (1983) *Lecture Proceedings*, pp. 12–29 (Birkhauser, Basil 1983); and H. Binding "Regeneration of Plants", *Plant Protoplasts*, pp. 21–73 (CRC Press, Bocaraton 1985). When transformation is of an organ part, regeneration can be from the plant calus, explants, organs or parts. Such methods for regeneration are also known to those skilled in the art. See, e.g., *Methods in Enzymology*, supra.; *Methods in Enzymology*, Vol. 118; and Klee et al. *Annual Review of Plant Physiology* 38:467–486.

Once plants have been regenerated, one or more plants are selected based upon a change in the floral phenotype. Such selection can be by visual observation of gross morphological changes in floral structure, by observation in a change in inflorescence or by observation in changes in microscopic floral structure, e.g., by electronmicroscopy and the like.

In those cases wherein a dominant phenotype is conferred upon transformation with a vector containing an agamous nucleic acid, the alteration in floral development can result in a sterile plant. In such cases, the plant can be propagated asexually by the taking of cuttings or by tissue culture techniques to produce multiple identical plants.

When the transformed plant is characterized by a recessive phenotype, e.g., when an antisense construct is used which is insufficient to confer the desired phenotype or which confers an intermediate phenotype which does not result in a sterile plant, such transformed plants can be inbred to homozygosity to obtain the desired phenotype. Such plants may then be asexually propagated or if such plants are not sterile, propagated sexually by way of seed.

As described in the examples, an agamous homolog from *Brassica napus* (BAG1) (SEQ ID NO:03) (a homolog of the *Arabdopsis agamous* gene (SEQ ID NO:01)) was constitutively expressed in transgenic tobacco plants. Such expression results in an AP2 phenotype. As used herein, an AP2 phenotype refers to a plant exhibiting a floral phenotype which is substantially similar to that observed in that species of plant when the endogenous AP2 gene has been mutated in such a way as to change floral characteristics.

Similarly, an AG phenotype refers to a floral phenotype substantially similar to that observed in the same species of plant wherein the endogenous agamous gene has been mutated to alter floral characteristics. Example 2 demonstrates that the AG phenotype was obtained when an antisense construct of an agamous gene was used to generate transgenic tobacco.

FIG. 10 depicts a model demonstrating how three classes of homeotic genes can specify organ identity for each of four whorls in a floral organ. A section through one-half of a flower primordium is shown with the outside of the flower to the left and the center of the flower to the right and the position of the whorls indicated. The distribution of the AP2, AP3/PI and AG gene products in fields A, B and C is shown for wild-type and AP2 mutant flowers as described by Bowman, et al., *Development* 112:1–20 (1991). Also shown in FIG. 10 is the distribution of gene products in plants transgenic for the 35S/BAG1 construct. The X through the AP2 gene product indicates that the activity of BAG1 in these whorls results in loss of AP2 function. The loss of the AP2 activity in whorls 1 and 2 as a consequence results in ectopic expression of the Nicotiana AG gene in these whorls as indicated by the arrow. As a consequence, the phenotype of the organs is shown below each diagram wherein SE=sepal; P=petal; ST=stamen and C=carpel.

Also shown in FIG. 10 is the AG phenotype which can be conferred by use of constructs utilizing antisense AG nucleic acids. This phenotype maintains the sepal and petal structure in whorls 1 and 2 but changes the stamen structure in whorl 3 to a petal-type structure and the carpel structure in whorl 4 to the sepal-type structure.

Given the confirmation of the AP2 phenotype using sense and the AG phenotype using antisense agamous nucleic acids, as described in the examples, it is apparent that various other phenotypes can be combined with the AP2 and/or AG phenotype to further modify floral development. Such other phenotypes include the AP3 and/or PI phenotypes which can be combined with the AP2 and/or AG phenotype to generate transgenic or mosaic plants having floral structure similar to those set forth in FIG. 11.

Thus, many useful phenotypes can be generated using agamous nucleic acids. Sense expression of an agamous nucleic acid within petals and sepals results in new flower configurations and reduced fertility. Expression of the same construct in pollen produces complete male sterility. Either antisense or co-suppression mechanisms using agamous nucleic acids results in the double flower (extra petals) phenotype. This same antisense or co-suppression mechanism can also result in complete male and female sterility. In addition, plants having such modified floral phenotypes can be used as model systems for further study of the formation and differentiation of reproductive tissue in plants.

Further, the agamous gene has been identified in plants from the genus Brassica, Arabidopsis and Nicotiana. Nicotiana is a member of the sub-class Archichlamydeae; Order Tubiflorae; whereas Brassica and Arabidopsis are members of the sub-class Metachlamydeae; Order Rhoeadales. Based on the known homology which exists between these agamous genes across sub-classes of dicots and the well-recognized agamous phenotype throughout diverse flowering plant taxa, the agamous gene clearly plays a fundamental role in flower development. The broad applicability of the use of agamous nucleic acid sequences in widely-divergent plant taxa is readily apparent from Example 1 where an agamous nucleic acid sequence from a member of the sub-class Metachlamydeae was used to confer an altered floral phenotype in the sub-class Archichlamydeae.

The following is presented by way of example and is not to be construed as a limitation on the scope of the invention. Further, all references referred to herein are expressly incorporated by reference.

EXAMPLE 1

Transgenic Tobacco Having an Altered Floral Phenotype (AP2)

This example describes the use of a vector encoding a constitutive promoter from Cauliflower Mosaic Virus operably linked to the sense strand of the agamous gene (SEQ ID NO:03) from *Brassica napus* to modify floral structure in *Nicotiana tabacum*.

Screening of cDNA Libraries

The *Brassica napus* cv Westar cDNA library, in the vector λZAPII (Stratagene), was made from RNA isolated from developing buds no longer than 5 mm. Approximately 200,000 plaques were screened with a gel purified DNA probe specific for the Arabidopsis AG cDNA (pCIT565) (Yanofsky, et al. *Nature* 346:35–39). This was radiolabelled using the Random Prime Labeling Kit from Boehringer Mannheim. Hybridizations were done at 55° C. in 5×SSPE, 5×Denhardt's solution, 0.5% SDS, 25 mg/ml salmon sperm DNA for 48 hours, followed by one room temperature and three 55° C. washes in 5×SSPE, 0.1% SDS.

Cloning and Sequence Analyses cDNAs were excised into pBluescript SK(+) (Stratagene) and subcloned into the vector pGEM7Zf(+) (Promega) for sequencing. Sequencing was performed using the US Biochemicals Sequeenase Version 2.0 kit according to the manufacturer's protocol. DNA and putative protein sequences were analyzed using the MacVector program from IBI.

RNA Analyses

RNA analyses were performed with total RNA isolated from flowers and leaves from the *Brassica napus* L. ssp. oleifera cv Westar plants according to procedures previously described (Crawford, et al. *PNAS* 83:8073–8076 (1986)). RNA was obtained from leaves and from immature flowers at various stages up to and including the stage at which the flowers are pollinated. 20 µg of RNA were loaded per lane. RNA was size fractionated on a 1% agarose gel containing 2.2M formaldehyde.

The gels were blotted onto Hybond-N Nylon membranes (Amersham) and hybridizations were performed as described (Chang, et al. *Proc. Natl. Acad. Sci. USA* 85:6856–6860 (1988)). The probe was a 687 bp BamHI-EcoRI fragment from the BAG1 cDNA cloned into pBluescript SK(+) (pKY14) (see FIG. 2).

Construction of CaMV35S/BAG1 Chimeric Gene

The EcoRI cDNA fragment containing the entire coding region for the BAG1 gene(SEQ ID NO:03) was inserted into the transcriptional fusion vector pMON530 (Rogers, et al. *Methods and Enzymology* 153:253–277 (1988)) and the resulting plasmid designated p35S/BAG1. This construct was introduced into Agrobacterium strain ASE and used to transform and regenerate *Nicotiana tabacum* var. Xanthi plants by standard methods (Horsch, et al. *Science* 227:1229–1231 (1985)). Two transgenic plants, 35S/BAG1.1 and 35S/BAG1.2 were studied in detail. Since these plants did not self pollinate, leaves were surface sterilized and placed into sterile culture to allow regeneration. All regenerated plants (12/12 for 35S/BAG1.1 and 14/14 for 35S/BAG1.2) displayed the same floral phenotypes as the parent plants. Although these plants never self pollinated, they could be successfully crossed with pollen from a wild-type plant. The resulting progeny from this cross segregated for the same floral phenotypes, indicating the phenotype is due to a dominant gene.

Scanning Electron Microscopy

Inflorescences were prepared and analyzed as described previously (Bowman, et al. *The Plant Cell* 1:37–52 (1989)).

Isolation of the Putative AG Homolog from Brassica

Genetic experiments suggest that three homeotic functions, A, B, and C, specify floral organ fate, and further, that the A and C functions are mutually antagonistic. In order to test the genetic model, we set out to generate transgenic tobacco plants that ectopically express the C function, which requires the AG gene in Arabidopsis. These experiments were designed to test if these functions are interchangeable between distantly related plant species, and to see if overexpression of AG is sufficient to suppress the A function, that is, if AG alone provides C function, or if there are other C function genes also necessary for negative regulation of the A function. Since the translation initiation codon has not been identified for the Arabidopsis AG gene (SEQ ID NO:011), making it difficult to construct transcriptional fusions, we isolated the putative AG homolog (SEQ ID NO:03) from the mustard *Brassica napus*, a member of the same family as Arabidopsis. A cDNA library constructed using RNA isolated from *Brassica napus* flowers was screened with a probe specific for the Arabidopsis AG gene (SEQ ID NO:01) under reduced stringency conditions, resulting in the isolation of the putative Brassica AG gene. The putative Brassica AG protein, BAG1 (SEQ ID NO:04), shares approximately 94% identical residues with the deduced Arabidopsis AG protein (SEQ ID NO:04) (FIG. 2). The deduced Arabidopsis AG protein (SEQ ID NO:05) is at least 286 amino acids in length with a calculated molecular mass of 32.75 kD and a pI of 9.61. However, since the translation initiation codon has not been identified, the actual AG protein may be slightly larger. The translation initiation codon for the BAG1 gene (SEQ ID NO:03) corresponds to amino acid 35 of the AG protein (SEQ ID NO:5). BAG1 (SEQ ID NO:03) codes for a putative 252 amino acid protein (SEQ. ID NO:04) of 28.78 kD and a pI of 9.48. AG (SEQ ID NO:05) and BAG1 (SEQ ID NO:04) share the same carboxy-terminal sequence. As an initial step towards determining the pattern of expression of the BAG1 gene (SEQ ID NO:03), RNA was isolated from leaves and flowers of *Brassica napus* and hybridized with a probe from the 3' portion of the BAG1 cDNA (to avoid cross-hybridization with other mRNAs containing the MADS box sequence, see FIG. 3A). As for AG (SEQ ID NO:010), the BAG1 gene (SEQ ID NO:03) is expressed preferentially in flowers, as no hybridization was observed to RNA isolated from leaves (FIG. 3BB).

Generation of Transgenic Tobacco Plants

The BAG1 (SEQ ID NO:03) coding region was transcriptionally fused to the 35S promoter from cauliflower mosaic virus (Odell et al. *Nature* 313:810–812 (1985)) and the resulting construct was introduced into *Nicotiana tabacum* var. Xanthi plants (FIG. 3A). Many independent transgenic plants were generated, and all the lines exhibited abnormal phenotypes ranging from weak to severe, presumably due to different levels of expression of the transgene. Two lines, one with a severe (designated 35S/BAG1.1) and one with an intermediate (designated 35S/BAG1.2) phenotype, were selected for these studies. DNA blotting analysis demonstrated that the introduced DNA was present in transgenic plants (FIG. 3C), and RNA blotting demonstrated that the transgene was expressed in both leaves and flowers (FIG. 3D). It should be noted that, although we refer to the 35S promoter (Odell, et al. (1985) supra.) as constitutive, the promoter region consists of a number of distinct elements that drive expression in different cell types (Benfey, et al. *Science* 250:959–966 (1990)).

Wild-type Flower Structure and Development

As a background to descriptions of the transgenic tobacco plants, a description of the appearance and development of wild-type flowers is necessary. Mature tobacco flowers are composed of four concentric whorls. The first whorl is occupied by five sepals which are connately fused for most of their length. Interior and alternate to the sepals are five petals which occupy the second whorl.

The petals are also connately fused with one another for the length of their lower region, called the tube. The unfused upper region, or limb, is pink in mature flowers, while the tube is white. The five stamens of the third whorl are adnately fused with the second whorl petals for much of the length of their filaments. The center of the flower, the fourth whorl, is occupied by a superior two-carpelled gynocium, with approximately 200 ovules developing from the central placental tissue. The ovary is topped with a long style capped with a two-lobed stigma with numerous papillae. Nectar is secreted from an orange colored ring of tissue at the base of the ovary.

The development of wild-type tobacco flowers has been described and divided into stages based on morphological markers (Hicks, et al. *Can. J. Bot.* 48:133–139 (1970); Koltunow, et al. *Plant Cell* 2:1201–1224 (1990)). We will extend the system of Koltunow, et al., whose stages begin when all four whorls of organ prunordia have arisen and begun to differentiate, to earlier events in floral development starting with an undifferentiated primordium (Table 1).

TABLE 1

| Stage | Morphological Markers |
|---|---|
| 1 (2) | Flower primordium distinct from bract primordium |
| 2 (3,4) | First sepal primordium arises |
| 3 (3,4) | All sepal primordia have formed |
| 4 (5) | Petal primordia are initiated |
| 5 (5,6) | Stamen primordia arise; growth between petals begins |
| 6 (7) | Carpel primordia arise; sepals almost closed; petals connately fused |
| 7 (8) | Sepals enclose bud; camels not quite fused; anthers and filaments distinct; locules becoming evident in anthers |
| 8 | Carpel primordia fused; stamen filaments elongated; petals equal in length with stamens; tapetum being formed |
| 9 | Petals enclose stamens; stigma forming on gynoecium |

TABLE 1-continued

| Stage | Morphological Markers |
|---|---|
| 11 | Style clearly elongated; ovule primordia evident |
| 12 | Petals approaching top of sepals |
| 15 | Petals longer than sepals; ovule primordia stalked |

Results for stages 6 to 15 are defined as in results from Koltunow et al. (1990), supra, and Evans et al. *Dev. Bio.* 136:273–283 (1989) as well as from our data, and stages have been numbered such that stage 1 represents the initial stage of flower development. Approximate Arabidopsis stages are from Smyth et al. *Plant Cell* 2:755–767 (1990). Only those stages relevant to these studies are shown.

Flower primordia arise either from the apical meristem (in the case of the apical terminal flower) or from a axillary meristem, in which case they are associated with a brat, which in turn has another axillary meristem (Stage 1, FIG. 4A). The first sign of morphological differentiation of the flower primordium is the appearance of a small buttress of cells, the first sepal primordium, that arises from the abaxial periphery of the flower primordium (Stage 2, FIGS. 4A, C). A second sepal primordium then arises in a position that is nearly opposite to that of the first (FIG. 4A). The remaining three sepal primordia form in close temporal succession (Stage 3). The growth of the later initiated sepal primordia lags slightly behind the earlier initiated ones (FIGS. 4A, B), until equalizing at about Stage 7. Five separate second whorl primordia arise in positions alternate with the first whorl primordia (stage 4, FIG. 4C), closely followed by the initiation of the five third whorl primordia develop into petals, connately fusing during stages 5 to 6 (FIG. 4E). The third whorl primordia develop into stamens, the anthers of which develop rapidly compared to the other floral organs, with lobes evident as early as Stage 7. The filaments remain relatively short during cellular differentiation of the anther (stages 7 to 12), after which the filaments elongate, their lower portions being adnately fused to the second whorl petal tube. Following the initiation of the second and third whorl organ primordia, the remaining floral meristem gives rise to the fourth whorl gynocium, which arises as two distinct, horseshoe-shaped primordia (stage 6, FIG. 4E). The two carpel primordia fuse soon after initiation resulting in the single ovary (stage 8, FIG. 4F). During this time the sepals have grown to enclose the inner floral organs (stage 7, FIG. 4F). Later stages, in which cellular differentiation of the organ primordia occurs, are described in detail in Koltunow, et al. *Plant Cell* 2:1201–1224 (1990) (FIG. 4G). Some of these stages are briefly outlined in Table 1, and will be discussed only where relevant. The individual cells that constitute each organ are characteristic of the organ type, such that both overall structure and cellular identity can be used as criteria for organ type. For example, the adaxial epidermal cells of petals are uniformly shaped and have characteristic cuticular thickenings (FIG. 4H), and ovules that develop on the central placental tissue in the fourth whorl carpels have a characteristic globular shape (FIG. 4I).

Flowers of Transgenic Plants

Two independent transgenic strains were analyzed, one that exhibited striking phenotypic changes relative to wild-type, 35S/BAG1.1, and a second that showed less severe alterations in phenotype, 35S/BAG1.2. In each case the major effects noted were alterations in floral structure, such as homeotic conversions of organ type and altered numbers and positions of floral organs. These effects are likely to result from ectopic BAG1 (SEQ ID NO:03) expression early in floral development, during stages 1 to 8. No changes in inflorescence structure were detected. In addition to the phenotypic effects early in flower development, we also describe alterations that are presumed to be due to ectopic expression of BAG1 later in development. Within each transgenic line, phenotypes varied such that the earliest flowers produced had less pronounced alterations compared to the flowers produced later. Thus, between the two lines, a continuum of phenotypes from nearly wild-type to a striking apetala2 phenotype was observed (FIG. 5C). Examples of inflorescences from a wild-type and transgenic plant with deviant flowers with an intermediate phenotype are shown (FIGS. 5D, E).

Early Development in Transgenic Plants 1. 35S/BAG1.1

The overall architecture of 35S/BAG1.1 flowers consists of capelloid organs in the first and fourth whorls and staminoid organs in the second and third whorls. The numbers and positions of the organs within whorls is usually not abnormal, except in the most severe cases (see below). The growth and fusion of the first whorl carpelloid organs usually impedes the growth of the organs of the interior whorls causing them to be morphologically distorted and senesce (and turn brown) prematurely. This precludes their growth beyond the height of the first whorl organs and the flowers resemble, at first glance, enlarged gynoecia (FIGS. 5B and 6F, G).

The development of 35S/BAG1.1 flowers diverges morphologically from that of wild-type as early as stages 2 to 3. The number, size, and location of the first whorl organ primordia may be altered (FIG. 6A). Although usually five separate primordia are initiated on the flank of the floral meristem, only four primordia are evident in some cases. The first whorl primordia soon fuse to each other forming a single structure resembling the outer walls of the wild-type gynoecium (FIG. 6G). The epidermal cells of this structure are carpelloid, and are lacking the numerous hairs associated with wild-type sepals. In addition, stigmatic papillae develop between the apices of the fused organs (FIG. 6H). At the base of the fuse first whorl organs is a ring of orange tissue that exudes nectar, like that of the wild-type gynoecium. Interior to the outer capelloid wall of the first whorl, a varying amount of placental tissue with ovule-like structures develops, and observations on developing flowers show that this tissue is also derived from the first whorl (FIG. 6I). The amount of placental tissue varies from almost none, such that the first whorl consists of merely a carpelloid shell similar to the outer walls of a wild-type ovary, to cases in which five discreet chambers of plancetal tissue develop, suggesting that each of the whorl organ primordia developed into an entire carpel rather than a wild-type sepal.

The organ primordia initiated in the second whorl are usually initiated in the normal positions (FIGS. 6B, C), but they subsequently differentiate into staminoid organs rather than the wild-type petals. The overall morphology of the second whorl organs ranges from petaloid stamens to carpelloid stamens, with distinct anther and filament regions easily observed (FIGS. 6D, E). The epidermal morphology is quite staminoid, but there may be higher density of hairs on their abaxial surface, characteristic of wild-type petals, and the tips may be petaloid in structure or may have stigmatic papillae. Pollen grains are not produced by these organs. The second whorl organs do not fuse as they do in wild-type.

In most cases, the third whorl primordia are initiated in the normal numbers and positions and each, similar to wild-type, develops into a staminoid organ (FIG. 6E). However, no pollen grains are produced by these organs, and thus, these plants are male sterile. In addition, the organs may be carpelloid, having stigmatic papillae at their tips, and often have other morphological alterations, such as changes in their shape, or ectopic outgrowths (FIGS. 6E, L). The initiation and external morphology of the fourth whorl carpels is usually normal, although if the third whorl organs are carpelloid, fusion may be observed between the third and fourth whorl organs. Later development of ovules from the placental tissue may be altered affecting the female fertility of the flowers (see below).

The above descriptions apply for most of the flowers produced on 35S/BAG1.1 plants. The earliest flowers to develop are often less affected and resemble those described for 35S/BAG1.2 plants (see below). In contrast, the later flowers produced may exhibit a more severe alteration of phenotype. They may consist of four whorls of carpelloid organs fused into a single structure and their pattern of organ primordia initiation is quite divergent from that of wild-type (FIG. 6J). There often appear to be four or fewer organs occupying each of the outer three whorls. Striking features of these flowers ar the abundance of stigmatic papillae at the tips of all floral organs and their tight fusion into a single entity that is not easily dissected (FIG. 6K). In some cases, the organs of the second and third whorls retain some degree of staminody morphologically, and these organs fail to fuse completely to the other organs. Again, the constriction of the fused outer whorl organs often causes distortions in the morphology and premature senescence of the organs occupying the inner whorls. This phenomenon occurs to such an extent that flowers of this phenotype have not been observed to develop to maturity, the entire flowers senescing before stage 15.

2. 35S/BAG1.2

The alterations observed in 35S/BAG1.2 flowers are more subtle than those observed in 35S/BAG1.1 flowers, and the development of 35S/BAG1.2 flowers rarely diverged from that of wild-type before stage 6. However, the trend of transformations is the same, with the first whorl organs developing carpelloid characteristics and the second whorl organs staminoid characteristics. The organs occupying the first whorl are carpelloid sepals. The initiation and development of these organs are similar to that of wild-type first whorl organs, except that the tips of the organs tend to be curled back rather than pointed upwards and stigmatic papillae develop at the top of the margins of fusion of the organs (FIG. 7A). The second whorl is occupied by organs which are morphologically intermediate between that of wild-type petals and stamens (FIG. 7B). The upper portion of the organs, which in wild-type would be the petal limb, fail to expand and enlarge as in the wild-type. Also in contrast to the wild-type, the second whorl organs fail to fuse to each other or to the staminoid organs of the third whorl. The third whorl is occupied by staminoid organs whose morphology is similar to that of wild-type stamens, although alterations in shape and presence of outgrowths are observed. No pollen grains are produced by these organs. The gynoecium that develops in the fourth whorl is again similar to that of wild-type flowers. However, in 29% (48/165) of flowers examined, the gynoecium was composed of three carpels, resulting in a three-lobed stigma, rather than the wild-type two carpels. Examination of developing flowers makes it clear that these carpels arise simultaneously (FIG. 7C). This phenomenon also occurs in 35S/BAG1.1 flowers.

Late Flower Development in Transgenic Plants

In Arabidopsis, AG is also expressed in late stages of flower organ differentiation (Bowman et al. *Plant Cell* 3:749–758 (1991)). Two primary alterations are observed that might be attributed to ectopic BAG1 (SEQ ID NO:03) expression late in tobacco flower development. Both effects are associated with gametophyte development and are observed in both transgenic lines, 35S/BAG1.1 and 35S/BAG1.2.

Firstly, the transgenic plants are male sterile. This is not due to a failure of dehiscence, but rather, a failure to produce any viable pollen grains. SEM analysis revealed that the locules of mature anthers of the transgenic flowers contained no visible pollen grains (data not shown). The second effect concerns development of the ovule from the placental tissue. In wild-type flowers approximately 200 ovules are produced from the central placental tissue of the fourth whorl gynoecium. In both transgenic lines the development of the ovules appears normal through approximately stage 15 when the ovule primordia become stalked, at which time they are as tall as they are wide. However, at this point, a small percentage of the ovule primordia in transgenic plants continue to elongate, developing into spaghetti-shaped structures, sometimes reaching over 10 mm in length (FIGS. 7 D, E). These aberrant structures often have stigmatic papillae at their tips, which are greenish in color, contrasting with the normally white ovules. The abnormal ovules arise frequently at the margins of the placenta and can be adjacent to ovules that appear to be morphologically normal (compare with FIG. 4I). That these plants can set seed at a low frequency when outcrossed indicates that not all ovules are functionally altered. The same type of transformation is also observed in the ovule primordia arising from the first whorl placental tissue of 35S/BAG1.1 flowers.

EXAMPLE 2

Production of AG Phenotype Using Vector Containing Antisense Agamous Construct

This example describes the use of the agamous gene from *Nicotiana tabacum* var. Xanthi in both sense and antisense orientations to produce the AP2 and AG phenotype respectively in transgenic tobacco.

A *Nicotiana tabacum* var. Xanthi cDNA library was prepared as described in Example 1. Plaques were screened with a gel purified DNA probe specific for the Arabidopsis AG cDNA.

DNA from a positive clone was digested with EcoR1 and the insert was cloned into the shuttle vector pMON530 in sense and antisense orientations such that transcription of the *Nicotiana agamous* gene (NAG1) was under control of the cauliflower mosaic virus 35S promoter. The DNA (SEQ ID NO:06) and amino acid (SEQ ID NO:07) of this agamous gene is shown in FIG. 11.

The sense and antisense vectors were used in separate experiments to transform *Nicotiana tabacum* var. Xanthi as described in Example 1. When the sense strand construct that was used, an AP2 phenotype similar to that described in Example 1 was obtained (results not shown).

Plants produced using the vector containing the antisense orientation of the *Nicotiana agamous* gene conferred an AG phenotype on the floral structure of the plants so obtained. A photograph of one of the flowers from such a plant is shown in FIG. 10. As can be seen, this flower contains a flower within a flower based upon the conversion of stamens to petals in this floral structure.

Having described the preferred embodiments of the present invention, it will appear to those of ordinary skill in the art that various modifications may be made to the disclosed embodiments, and that such modifications are intended to be within the scope of the present invention.

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 1457 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 416..1270

( x i ) SEQUENCE DESCRIPTION: SEQ ID NO:1:

```
CTAAATGTAC  TGAAAAGAAA  CACCAGTTTA  ATTAATTATA  CTTTCCTCAC  ATATAACTAT          60

CAACCAAGTA  CAAAACTTTT  GTCAATTCTC  AAAATCAACT  TTCACCACAT  AATTATCTAA         120

CATGTGTATG  TTCCAAAACC  AGTTTAAATG  AATTACTTTT  CAGAAAATAC  ATGTATATTA         180

ACTCTATCTA  ATAAAGAAGA  AACACATACT  TATCTCATAG  ATTCCATTCA  TAAAACTATG         240

CTTTAGTGAG  TAAGAAAACC  AGTAATCAAA  CACAAATTGA  CAAGACACTA  TATGGATGTA         300

AAAAGTGGGG  AAAATATGGT  GATAAATAGT  AGAGAAAATT  AAAAAGAAAA  AATAATATTC         360

CTTTATAAAT  GTATATACCC  ATCTCTTCAC  CAGCACAACC  TTACCTTCCA  TTTTC CAT          418
                                                                  His
                                                                   1

TTT CTG CAA CTT CTC CAA ATC TCA TAC TTT CCA GAA AAT CAT TTT CCC                466
Phe Leu Gln Leu Leu Gln Ile Ser Tyr Phe Pro Glu Asn His Phe Pro
              5                  10                 15

AAG AAA AAT AAA ACT TTC CCC TTT GTT CTT CTC CCC CCA ACA GCA ATC                514
Lys Lys Asn Lys Thr Phe Pro Phe Val Leu Leu Pro Pro Thr Ala Ile
         20                  25                 30

ACG GCG TAC CAA TCG GAG CTA GGA GGA GAT TCC TCT CCC TTG AGG AAA                562
Thr Ala Tyr Gln Ser Glu Leu Gly Gly Asp Ser Ser Pro Leu Arg Lys
     35                  40                 45

TCT GGG AGA GGA AAG ATC GAA ATC AAA CGG ATC GAG AAC ACA ACG AAT                610
Ser Gly Arg Gly Lys Ile Glu Ile Lys Arg Ile Glu Asn Thr Thr Asn
 50                  55                 60                 65

CGT CAA GTC ACT TTT TGC AAA CGT AGA AAT GGT TTG CTC AAG AAA GCT                658
Arg Gln Val Thr Phe Cys Lys Arg Arg Asn Gly Leu Leu Lys Lys Ala
                     70                 75                 80

TAC GAG CTC TCT GTT CTC TGT GAT GCT GAA GTC GCA CTC ATC GTT TTC                706
Tyr Glu Leu Ser Val Leu Cys Asp Ala Glu Val Ala Leu Ile Val Phe
                 85                 90                 95

TCT AGC CGT GGT CGT CTC TAT GAG TAC TCT AAC AAC AGT GTA AAA GGT                754
Ser Ser Arg Gly Arg Leu Tyr Glu Tyr Ser Asn Asn Ser Val Lys Gly
             100                 105                110

ACT ATT GAG AGG TAC AAG AAG GCA ATA TCG GAC AAT TCT AAC ACC GGA                802
Thr Ile Glu Arg Tyr Lys Lys Ala Ile Ser Asp Asn Ser Asn Thr Gly
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | 115 |     |     |     |     | 120 |     |     |     |     | 125 |     |     |     |     |      |
| TCG | GTG | GCA | GAA | ATT | AAT | GCA | CAG | TAT | TAT | CAA | CAA | GAA | TCA | GCC | AAA | 850  |
| Ser | Val | Ala | Glu | Ile | Asn | Ala | Gln | Tyr | Tyr | Gln | Gln | Glu | Ser | Ala | Lys |      |
| 130 |     |     |     | 135 |     |     |     |     | 140 |     |     |     |     |     | 145 |      |
| TTG | CGT | CAA | CAA | ATT | ATC | AGC | ATA | CAA | AAC | TCC | AAC | AGG | CAA | TTG | ATG | 898  |
| Leu | Arg | Gln | Gln | Ile | Ile | Ser | Ile | Gln | Asn | Ser | Asn | Arg | Gln | Leu | Met |      |
|     |     |     |     |     | 150 |     |     |     |     | 155 |     |     |     |     | 160 |      |
| GGT | GAG | ACG | ATA | GGG | TCA | ATG | TCT | CCC | AAA | GAG | CTC | AGG | AAC | TTG | GAA | 946  |
| Gly | Glu | Thr | Ile | Gly | Ser | Met | Ser | Pro | Lys | Glu | Leu | Arg | Asn | Leu | Glu |      |
|     |     |     | 165 |     |     |     |     | 170 |     |     |     |     | 175 |     |     |      |
| GGC | AGA | TTA | GAG | AGA | AGT | ATT | ACC | CGA | ATC | CGA | TCC | AAG | AAG | AAT | GAG | 994  |
| Gly | Arg | Leu | Glu | Arg | Ser | Ile | Thr | Arg | Ile | Arg | Ser | Lys | Lys | Asn | Glu |      |
|     |     | 180 |     |     |     |     | 185 |     |     |     |     | 190 |     |     |     |      |
| CTC | TTA | TTT | TCT | GAA | ATC | GAC | TAC | ATG | CAG | AAA | AGA | GAA | GTT | GAT | TTG | 1042 |
| Leu | Leu | Phe | Ser | Glu | Ile | Asp | Tyr | Met | Gln | Lys | Arg | Glu | Val | Asp | Leu |      |
|     | 195 |     |     |     |     | 200 |     |     |     |     | 205 |     |     |     |     |      |
| CAT | AAC | GAT | AAC | CAG | ATT | CTT | CGT | GCA | AAG | ATA | GCT | GAA | AAT | GAG | AGG | 1090 |
| His | Asn | Asp | Asn | Gln | Ile | Leu | Arg | Ala | Lys | Ile | Ala | Glu | Asn | Glu | Arg |      |
| 210 |     |     |     |     | 215 |     |     |     |     | 220 |     |     |     |     | 225 |      |
| AAC | AAT | CCG | AGT | ATA | AGT | CTA | ATG | CCA | GGA | GGA | TCT | AAC | TAC | GAG | CAG | 1138 |
| Asn | Asn | Pro | Ser | Ile | Ser | Leu | Met | Pro | Gly | Gly | Ser | Asn | Tyr | Glu | Gln |      |
|     |     |     |     | 230 |     |     |     |     | 235 |     |     |     |     | 240 |     |      |
| CTT | ATG | CCA | CCA | CCT | CAA | ACG | CAA | TCT | CAA | CCG | TTT | GAT | TCA | CGG | AAT | 1186 |
| Leu | Met | Pro | Pro | Pro | Gln | Thr | Gln | Ser | Gln | Pro | Phe | Asp | Ser | Arg | Asn |      |
|     |     |     | 245 |     |     |     |     | 250 |     |     |     |     | 255 |     |     |      |
| TAT | TTC | CAA | GTC | GCG | GCA | TTG | CAA | CCT | AAC | AAT | CAC | CAT | TAC | TCA | TCC | 1234 |
| Tyr | Phe | Gln | Val | Ala | Ala | Leu | Gln | Pro | Asn | Asn | His | His | Tyr | Ser | Ser |      |
|     |     | 260 |     |     |     |     | 265 |     |     |     |     | 270 |     |     |     |      |
| GCC | GGT | CGC | CAA | GAC | CAA | ACC | GCT | CTC | CAG | TTA | GTG | TAATATTGGC |   |   |   | 1280 |
| Ala | Gly | Arg | Gln | Asp | Gln | Thr | Ala | Leu | Gln | Leu | Val |     |     |     |     |      |
| 275 |     |     |     |     | 280 |     |     |     |     | 285 |     |     |     |     |     |      |

```
TGAAGGAAAT GGCCTGGAGT GAATAAAAAC CAGAATTGGG TTGAGCAAGC AATATAAAGC    1340

TAATGCATGT TATATATATA TTTATCCCAT GAATGTTGTA TCAGTGAATT CTTATGCTTA    1400

TGTTGATGTG AAATTAATAT CTTAAAGACA TGTCATTAAT GTGCTTAATT TGCTTCA      1457
```

( 2 ) INFORMATION FOR SEQ ID NO:2:

( i ) SEQUENCE CHARACTERISTICS:
        ( A ) LENGTH: 285 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|     |     |     |     |     |     |     |     |     |     |     |     |     |     |     |
| --- | --- | --- | --- | --- | --- | --- | --- | --- | --- | --- | --- | --- | --- | --- |
| His | Phe | Leu | Gln | Leu | Leu | Gln | Ile | Ser | Tyr | Phe | Pro | Glu | Asn | His | Phe |
| 1   |     |     |     | 5   |     |     |     |     | 10  |     |     |     |     | 15  |     |
| Pro | Lys | Lys | Asn | Lys | Thr | Phe | Pro | Phe | Val | Leu | Leu | Pro | Pro | Thr | Ala |
|     |     |     | 20  |     |     |     |     | 25  |     |     |     |     | 30  |     |     |
| Ile | Thr | Ala | Tyr | Gln | Ser | Glu | Leu | Gly | Gly | Asp | Ser | Ser | Pro | Leu | Arg |
|     |     | 35  |     |     |     |     | 40  |     |     |     |     | 45  |     |     |     |
| Lys | Ser | Gly | Arg | Gly | Lys | Ile | Glu | Ile | Lys | Arg | Ile | Glu | Asn | Thr | Thr |
|     | 50  |     |     |     |     | 55  |     |     |     |     | 60  |     |     |     |     |
| Asn | Arg | Gln | Val | Thr | Phe | Cys | Lys | Arg | Arg | Asn | Gly | Leu | Leu | Lys | Lys |
| 65  |     |     |     |     | 70  |     |     |     |     | 75  |     |     |     |     | 80  |
| Ala | Tyr | Glu | Leu | Ser | Val | Leu | Cys | Asp | Ala | Glu | Val | Ala | Leu | Ile | Val |
|     |     |     |     | 85  |     |     |     |     | 90  |     |     |     |     | 95  |     |
| Phe | Ser | Ser | Arg | Gly | Arg | Leu | Tyr | Glu | Tyr | Ser | Asn | Asn | Ser | Val | Lys |
|     |     |     | 100 |     |     |     |     | 105 |     |     |     |     | 110 |     |     |

| Gly | Thr | Ile | Glu | Arg | Tyr | Lys | Lys | Ala | Ile | Ser | Asp | Asn | Ser | Asn | Thr |
|---|---|---|---|---|---|---|---|---|---|---|---|---|---|---|---|
|  |  | 115 |  |  |  |  | 120 |  |  |  |  | 125 |  |  |  |

| Gly | Ser | Val | Ala | Glu | Ile | Asn | Ala | Gln | Tyr | Tyr | Gln | Gln | Glu | Ser | Ala |
|---|---|---|---|---|---|---|---|---|---|---|---|---|---|---|---|
|  | 130 |  |  |  |  | 135 |  |  |  |  | 140 |  |  |  |  |

| Lys | Leu | Arg | Gln | Gln | Ile | Ile | Ser | Ile | Gln | Asn | Ser | Asn | Arg | Gln | Leu |
|---|---|---|---|---|---|---|---|---|---|---|---|---|---|---|---|
| 145 |  |  |  |  | 150 |  |  |  |  | 155 |  |  |  |  | 160 |

| Met | Gly | Glu | Thr | Ile | Gly | Ser | Met | Ser | Pro | Lys | Glu | Leu | Arg | Asn | Leu |
|---|---|---|---|---|---|---|---|---|---|---|---|---|---|---|---|
|  |  |  |  | 165 |  |  |  |  | 170 |  |  |  |  | 175 |  |

| Glu | Gly | Arg | Leu | Glu | Arg | Ser | Ile | Thr | Arg | Ile | Arg | Ser | Lys | Lys | Asn |
|---|---|---|---|---|---|---|---|---|---|---|---|---|---|---|---|
|  |  |  | 180 |  |  |  |  | 185 |  |  |  |  | 190 |  |  |

| Glu | Leu | Leu | Phe | Ser | Glu | Ile | Asp | Tyr | Met | Gln | Lys | Arg | Glu | Val | Asp |
|---|---|---|---|---|---|---|---|---|---|---|---|---|---|---|---|
|  |  | 195 |  |  |  |  | 200 |  |  |  |  | 205 |  |  |  |

| Leu | His | Asn | Asp | Asn | Gln | Ile | Leu | Arg | Ala | Lys | Ile | Ala | Glu | Asn | Glu |
|---|---|---|---|---|---|---|---|---|---|---|---|---|---|---|---|
|  | 210 |  |  |  |  | 215 |  |  |  |  | 220 |  |  |  |  |

| Arg | Asn | Asn | Pro | Ser | Ile | Ser | Leu | Met | Pro | Gly | Gly | Ser | Asn | Tyr | Glu |
|---|---|---|---|---|---|---|---|---|---|---|---|---|---|---|---|
| 225 |  |  |  |  | 230 |  |  |  |  | 235 |  |  |  |  | 240 |

| Gln | Leu | Met | Pro | Pro | Pro | Gln | Thr | Gln | Ser | Gln | Pro | Phe | Asp | Ser | Arg |
|---|---|---|---|---|---|---|---|---|---|---|---|---|---|---|---|
|  |  |  |  | 245 |  |  |  |  | 250 |  |  |  |  | 255 |  |

| Asn | Tyr | Phe | Gln | Val | Ala | Ala | Leu | Gln | Pro | Asn | Asn | His | His | Tyr | Ser |
|---|---|---|---|---|---|---|---|---|---|---|---|---|---|---|---|
|  |  |  | 260 |  |  |  |  | 265 |  |  |  |  | 270 |  |  |

| Ser | Ala | Gly | Arg | Gln | Asp | Gln | Thr | Ala | Leu | Gln | Leu | Val |
|---|---|---|---|---|---|---|---|---|---|---|---|---|
|  |  | 275 |  |  |  |  | 280 |  |  |  |  | 285 |

( 2 ) INFORMATION FOR SEQ ID NO:3:

( i ) SEQUENCE CHARACTERISTICS:
        ( A ) LENGTH: 1097 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 126..884

( x i ) SEQUENCE DESCRIPTION: SEQ ID NO:3:

```
CAATCAACAA CTTCACCCTT CCATTTTCTG CAACTTCTCC AAATCTCATA CTTTCCAGAA      60

AATCATTTTC CAAGAGAAA  TAAAACTTTC CTCTTTGTTC ATCTCTCTTC CCCCCAACAG     120

CAAAC ATG GCT TAC CAA ATG GAG CTA GGA GGA GAA TCC TCT CCA CAA         167
      Met Ala Tyr Gln Met Glu Leu Gly Gly Glu Ser Ser Pro Gln
        1               5                  10

AGG AAA GCT GGG AGA GGA AAG ATC GAA ATA AAA CGG ATC GAG AAC ACA       215
Arg Lys Ala Gly Arg Gly Lys Ile Glu Ile Lys Arg Ile Glu Asn Thr
 15              20                  25                  30

ACG AAC CGT CAA GTT ACT TTC TGC AAA CGC AGA AAT GGT TTG CTC AAG       263
Thr Asn Arg Gln Val Thr Phe Cys Lys Arg Arg Asn Gly Leu Leu Lys
                 35                  40                  45

AAA GCT TAC GAA CTC TCT GTT CTT TGT GAT GCT GAA GTC GCA CTC ATT       311
Lys Ala Tyr Glu Leu Ser Val Leu Cys Asp Ala Glu Val Ala Leu Ile
             50                  55                  60

GTC TTC TCT AGC CGT GGC CGT CTC TAT GAG TAC TCA AAC AAC AGT GTA       359
Val Phe Ser Ser Arg Gly Arg Leu Tyr Glu Tyr Ser Asn Asn Ser Val
         65                  70                  75

AAA GGG ACA ATT GAG AGG TAC AAG AAA GCA ATA TCG GAT AAT TCT AAC       407
Lys Gly Thr Ile Glu Arg Tyr Lys Lys Ala Ile Ser Asp Asn Ser Asn
     80                  85                  90

ACC GGA TCC GTG GCA GAA ATT AAT GCA CAG TAT TAT CAA CAA GAA TCT       455
```

| | | | | | | | | | | | | | | | |
|---|---|---|---|---|---|---|---|---|---|---|---|---|---|---|---|
| Thr | Gly | Ser | Val | Ala | Glu | Ile | Asn | Ala | Gln | Tyr | Tyr | Gln | Gln | Glu | Ser |
| 95 | | | | 100 | | | | | 105 | | | | | | 110 |

```
GCC AAA TTG CGT CAA CAA ATT ATC AGC ATA CAG AAC TCG AAC AGG CAA     503
Ala Lys Leu Arg Gln Gln Ile Ile Ser Ile Gln Asn Ser Asn Arg Gln
                115                 120                 125

TTG ATG GGT GAG ACG ATT GGG TCA ATG TCT CCC AAA GAG CTC AGG AAC     551
Leu Met Gly Glu Thr Ile Gly Ser Met Ser Pro Lys Glu Leu Arg Asn
            130                 135                 140

TTG GAA GGC AGA TTA GAC AGA AGT GTT AAT CGA ATC CGA TCC AAG AAG     599
Leu Glu Gly Arg Leu Asp Arg Ser Val Asn Arg Ile Arg Ser Lys Lys
            145                 150                 155

AAC GAA CTC TTA TTC GCC GAA ATT GAC TAC ATG CAG AAG AGA GAA GTT     647
Asn Glu Leu Leu Phe Ala Glu Ile Asp Tyr Met Gln Lys Arg Glu Val
    160                 165                 170

GAT TTG CAT AAC GAT AAC CAG CTT CTT CGT GCT AAG ATA GCT GAA AAT     695
Asp Leu His Asn Asp Asn Gln Leu Leu Arg Ala Lys Ile Ala Glu Asn
175                 180                 185                 190

GAG AGG AAC AAT CCA AGT ATG AGT CTG ATG CCA GGA GGA TCT AAC TAC     743
Glu Arg Asn Asn Pro Ser Met Ser Leu Met Pro Gly Gly Ser Asn Tyr
                195                 200                 205

GAG CAG ATC ATG CCA CCG CCT CAA ACG CAA CCT CAA CCG TTT GAC TCA     791
Glu Gln Ile Met Pro Pro Pro Gln Thr Gln Pro Gln Pro Phe Asp Ser
            210                 215                 220

CGG AAC TAT TTC CAA GTC GCG GCA TTG CAA CCT AAC AAT CAC CAT TAC     839
Arg Asn Tyr Phe Gln Val Ala Ala Leu Gln Pro Asn Asn His His Tyr
            225                 230                 235

TCA TCC GCA GGT CGC GAA GAC CAA ACC GCT CTT CAG TTA GTG TAATATTGGC  891
Ser Ser Ala Gly Arg Glu Asp Gln Thr Ala Leu Gln Leu Val
    240                 245                 250

TGAAGCATGA AGGAGCAAGG ACTGAATAAA AACCAGAACT GGGTTAAGGA ACGAGCGATA   951

TAAAGCTGAT GCACTGTTAT AAAAATATTT ATATATTTAT TTCACGAATG TTGTGTCCAT  1011

GCTTTCTACA TTTTATTTAA ATTGCTTATG TTGATGTGAA ATTAATATCT TAAAAGACAT  1071

GTGATTAATG TGCTTAATTT GTTTCG                                      1097
```

( 2 ) INFORMATION FOR SEQ ID NO:4:

( i ) SEQUENCE CHARACTERISTICS:
        ( A ) LENGTH: 252 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | | |
|---|---|---|---|---|---|---|---|---|---|---|---|---|---|---|---|
| Met | Ala | Tyr | Gln | Met | Glu | Leu | Gly | Gly | Glu | Ser | Ser | Pro | Gln | Arg | Lys |
| 1 | | | | 5 | | | | | 10 | | | | | 15 | |
| Ala | Gly | Arg | Gly | Lys | Ile | Glu | Ile | Lys | Arg | Ile | Glu | Asn | Thr | Thr | Asn |
| | | | 20 | | | | 25 | | | | | 30 | | | |
| Arg | Gln | Val | Thr | Phe | Cys | Lys | Arg | Arg | Asn | Gly | Leu | Leu | Lys | Lys | Ala |
| | | | 35 | | | 40 | | | | | 45 | | | | |
| Tyr | Glu | Leu | Ser | Val | Leu | Cys | Asp | Ala | Glu | Val | Ala | Leu | Ile | Val | Phe |
| | 50 | | | | 55 | | | | 60 | | | | | | |
| Ser | Ser | Arg | Gly | Arg | Leu | Tyr | Glu | Tyr | Ser | Asn | Asn | Ser | Val | Lys | Gly |
| 65 | | | | 70 | | | | 75 | | | | | | 80 | |
| Thr | Ile | Glu | Arg | Tyr | Lys | Lys | Ala | Ile | Ser | Asp | Asn | Ser | Asn | Thr | Gly |
| | | | 85 | | | | 90 | | | | | 95 | | | |
| Ser | Val | Ala | Glu | Ile | Asn | Ala | Gln | Tyr | Tyr | Gln | Gln | Glu | Ser | Ala | Lys |
| | | 100 | | | | 105 | | | | | 110 | | | | |

| Leu | Arg | Gln | Gln | Ile | Ile | Ser | Ile | Gln | Asn | Ser | Asn | Arg | Gln | Leu | Met |
|||||||||||||||||
|     |     |     | 115 |     |     |     |     | 120 |     |     |     |     | 125 |     |     |

| Gly | Glu | Thr | Ile | Gly | Ser | Met | Ser | Pro | Lys | Glu | Leu | Arg | Asn | Leu | Glu |
|||||||||||||||||
|     |     | 130 |     |     |     |     | 135 |     |     |     |     | 140 |     |     |     |

| Gly | Arg | Leu | Asp | Arg | Ser | Val | Asn | Arg | Ile | Arg | Ser | Lys | Lys | Asn | Glu |
|||||||||||||||||
| 145 |     |     |     |     | 150 |     |     |     |     | 155 |     |     |     |     | 160 |

| Leu | Leu | Phe | Ala | Glu | Ile | Asp | Tyr | Met | Gln | Lys | Arg | Glu | Val | Asp | Leu |
|||||||||||||||||
|     |     |     |     | 165 |     |     |     |     | 170 |     |     |     |     | 175 |     |

| His | Asn | Asp | Asn | Gln | Leu | Leu | Arg | Ala | Lys | Ile | Ala | Glu | Asn | Glu | Arg |
|||||||||||||||||
|     |     |     | 180 |     |     |     |     | 185 |     |     |     |     | 190 |     |     |

| Asn | Asn | Pro | Ser | Met | Ser | Leu | Met | Pro | Gly | Gly | Ser | Asn | Tyr | Glu | Gln |
|||||||||||||||||
|     |     |     | 195 |     |     |     |     | 200 |     |     |     |     | 205 |     |     |

| Ile | Met | Pro | Pro | Pro | Gln | Thr | Gln | Pro | Gln | Pro | Phe | Asp | Ser | Arg | Asn |
|||||||||||||||||
|     |     | 210 |     |     |     |     | 215 |     |     |     |     | 220 |     |     |     |

| Tyr | Phe | Gln | Val | Ala | Ala | Leu | Gln | Pro | Asn | Asn | His | His | Tyr | Ser | Ser |
|||||||||||||||||
| 225 |     |     |     |     | 230 |     |     |     |     | 235 |     |     |     |     | 240 |

| Ala | Gly | Arg | Glu | Asp | Gln | Thr | Ala | Leu | Gln | Leu | Val |
|||||||||||
|     |     |     |     | 245 |     |     |     |     | 250 |     |     |

( 2 ) INFORMATION FOR SEQ ID NO:5:

( i ) SEQUENCE CHARACTERISTICS:
        ( A ) LENGTH: 252 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

| Thr | Ala | Tyr | Gln | Ser | Glu | Leu | Gly | Gly | Asp | Ser | Ser | Pro | Leu | Arg | Lys |
|||||||||||||||||
| 1   |     |     |     | 5   |     |     |     |     | 10  |     |     |     |     | 15  |     |

| Ser | Gly | Arg | Gly | Lys | Ile | Glu | Ile | Lys | Arg | Ile | Glu | Asn | Thr | Thr | Asn |
|||||||||||||||||
|     |     |     | 20  |     |     |     |     | 25  |     |     |     |     | 30  |     |     |

| Arg | Gln | Val | Thr | Phe | Cys | Lys | Arg | Arg | Asn | Gly | Leu | Leu | Lys | Lys | Ala |
|||||||||||||||||
|     |     |     | 35  |     |     |     |     | 40  |     |     |     |     | 45  |     |     |

| Tyr | Glu | Leu | Ser | Val | Leu | Cys | Asp | Ala | Glu | Val | Ala | Leu | Ile | Val | Phe |
|||||||||||||||||
|     | 50  |     |     |     |     | 55  |     |     |     |     | 60  |     |     |     |     |

| Ser | Ser | Arg | Gly | Arg | Leu | Tyr | Glu | Tyr | Ser | Asn | Asn | Ser | Val | Lys | Gly |
|||||||||||||||||
| 65  |     |     |     |     | 70  |     |     |     |     | 75  |     |     |     |     | 80  |

| Thr | Ile | Glu | Arg | Tyr | Lys | Lys | Ala | Ile | Ser | Asp | Asn | Ser | Asn | Thr | Gly |
|||||||||||||||||
|     |     |     |     | 85  |     |     |     |     | 90  |     |     |     |     | 95  |     |

| Ser | Val | Ala | Glu | Ile | Asn | Ala | Gln | Tyr | Tyr | Gln | Gln | Glu | Ser | Ala | Lys |
|||||||||||||||||
|     |     |     | 100 |     |     |     |     | 105 |     |     |     |     | 110 |     |     |

| Leu | Arg | Gln | Gln | Ile | Ile | Ser | Ile | Gln | Asn | Ser | Asn | Arg | Gln | Leu | Met |
|||||||||||||||||
|     |     |     | 115 |     |     |     |     | 120 |     |     |     |     | 125 |     |     |

| Gly | Glu | Thr | Ile | Gly | Ser | Met | Ser | Pro | Lys | Glu | Leu | Arg | Asn | Leu | Glu |
|||||||||||||||||
|     |     | 130 |     |     |     |     | 135 |     |     |     |     | 140 |     |     |     |

| Gly | Arg | Leu | Glu | Arg | Ser | Ile | Thr | Arg | Ile | Arg | Ser | Lys | Lys | Asn | Glu |
|||||||||||||||||
| 145 |     |     |     |     | 150 |     |     |     |     | 155 |     |     |     |     | 160 |

| Leu | Leu | Phe | Ser | Glu | Ile | Asp | Tyr | Met | Gln | Lys | Arg | Glu | Val | Asp | Leu |
|||||||||||||||||
|     |     |     |     | 165 |     |     |     |     | 170 |     |     |     |     | 175 |     |

| His | Asn | Asp | Asn | Gln | Ile | Leu | Arg | Ala | Lys | Ile | Ala | Glu | Asn | Glu | Arg |
|||||||||||||||||
|     |     |     | 180 |     |     |     |     | 185 |     |     |     |     | 190 |     |     |

| Asn | Asn | Pro | Ser | Ile | Ser | Leu | Met | Pro | Gly | Gly | Ser | Asn | Tyr | Glu | Gln |
|||||||||||||||||
|     |     |     | 195 |     |     |     |     | 200 |     |     |     |     | 205 |     |     |

| Leu | Met | Pro | Pro | Pro | Gln | Thr | Gln | Ser | Gln | Pro | Phe | Asp | Ser | Arg | Asn |

```
                  210                        215                         220
        Tyr  Phe  Gln  Val  Ala  Ala  Leu  Gln  Pro  Asn  Asn  His  His  Tyr  Ser  Ser
        225                      230                      235                       240

Ala  Gly  Arg  Gln  Asp  Gln  Thr  Ala  Leu  Gln  Leu  Val
                            245                      250
```

( 2 ) INFORMATION FOR SEQ ID NO:6:

( i ) SEQUENCE CHARACTERISTICS:
        ( A ) LENGTH: 1125 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 110..853

( x i ) SEQUENCE DESCRIPTION: SEQ ID NO:6:

```
GAATTCCATA  TATCTATCCT  CTGCAGATTA  ATTTGCAAGG  AAGAACTAAA  AACTTTCTGT         60

ACTCTCTATT  TTCATCTTCC  AACCCTTTCT  TTCCTTACCA  GGTGAAAGT  ATG  GAC           115
                                                            Met  Asp
                                                             1

TTC  CAA  AGT  GAT  CTA  ACA  AGA  GAG  ATC  TCT  CCA  CAA  AGG  AAA  CTG  GGA    163
Phe  Gln  Ser  Asp  Leu  Thr  Arg  Glu  Ile  Ser  Pro  Gln  Arg  Lys  Leu  Gly
               5                        10                       15

AGA  GGA  AAG  ATT  GAG  ATC  AAA  CGG  ATC  GAA  AAC  ACA  ACG  AAT  CGT  CAA    211
Arg  Gly  Lys  Ile  Glu  Ile  Lys  Arg  Ile  Glu  Asn  Thr  Thr  Asn  Arg  Gln
          20                        25                       30

GTC  ACT  TTC  TGC  AAG  AGA  CGC  AAT  GGT  TTA  CTC  AAA  AAG  GCC  TAT  GAA    259
Val  Thr  Phe  Cys  Lys  Arg  Arg  Asn  Gly  Leu  Leu  Lys  Lys  Ala  Tyr  Glu
35                        40                       45                       50

TTA  TCT  GTG  CTC  TGT  GAT  GCT  GAG  GTT  GCT  TTG  ATT  GTC  TTC  TCA  AGC    307
Leu  Ser  Val  Leu  Cys  Asp  Ala  Glu  Val  Ala  Leu  Ile  Val  Phe  Ser  Ser
                    55                        60                       65

AGA  GGC  AGA  CTC  TAT  GAG  TAT  GCC  AAC  AAC  AGT  GTG  AAA  GCA  ACA  ATT    355
Arg  Gly  Arg  Leu  Tyr  Glu  Tyr  Ala  Asn  Asn  Ser  Val  Lys  Ala  Thr  Ile
               70                        75                       80

GAG  AGG  TAC  AAG  AAA  GCT  TGT  TCA  GAT  TCC  TCA  AAC  ACT  GGT  TCA  ATT    403
Glu  Arg  Tyr  Lys  Lys  Ala  Cys  Ser  Asp  Ser  Ser  Asn  Thr  Gly  Ser  Ile
          85                        90                       95

TCC  GAG  GCC  AAT  GCT  CAG  TAT  TAT  CAG  CAA  GAA  GCC  TCC  AAA  CTG  CGC    451
Ser  Glu  Ala  Asn  Ala  Gln  Tyr  Tyr  Gln  Gln  Glu  Ala  Ser  Lys  Leu  Arg
100                      105                      110

GCA  CAA  ATT  GGA  AAT  CTG  CAG  AAT  CAG  AAC  AGG  AAC  ATG  TTG  GGT  GAA    499
Ala  Gln  Ile  Gly  Asn  Leu  Gln  Asn  Gln  Asn  Arg  Asn  Met  Leu  Gly  Glu
115                      120                      125                      130

TCA  CTG  GCT  GCA  CTG  AGC  CTC  AGA  GAT  CTG  AAG  AAT  CTG  GAA  CAA  AAA    547
Ser  Leu  Ala  Ala  Leu  Ser  Leu  Arg  Asp  Leu  Lys  Asn  Leu  Glu  Gln  Lys
                    135                      140                      145

ATT  GAA  AAA  GGC  ATT  AGC  AAA  ATC  AGA  TCC  AAA  AAG  AAT  GAG  CTG  CTG    595
Ile  Glu  Lys  Gly  Ile  Ser  Lys  Ile  Arg  Ser  Lys  Lys  Asn  Glu  Leu  Leu
               150                      155                      160

TTT  GCT  GAA  ATT  GAG  TAC  ATG  CAG  AAG  AGG  GAA  ATT  GAT  TTA  CAC  AAC    643
Phe  Ala  Glu  Ile  Glu  Tyr  Met  Gln  Lys  Arg  Glu  Ile  Asp  Leu  His  Asn
          165                      170                      175

AAC  AAT  CAG  TAC  CTG  AGA  GCA  AAG  ATT  GCT  GAA  ACT  GAG  AGA  GCT  CAG    691
Asn  Asn  Gln  Tyr  Leu  Arg  Ala  Lys  Ile  Ala  Glu  Thr  Glu  Arg  Ala  Gln
180                      185                      190

CAG  CAG  CAG  CAG  CAG  CAG  CAG  ATG  AAC  TTG  ATG  CCA  GGG  AGT  TCA  AGC    739
```

|     |     |     |     |     |     |     |     |     |     |     |     |     |     |     |     |
|---|---|---|---|---|---|---|---|---|---|---|---|---|---|---|---|
| Gln | Gln | Gln | Gln | Gln | Gln | Gln | Met | Asn | Leu | Met | Pro | Gly | Ser | Ser | Ser |
| 195 |     |     |     |     | 200 |     |     |     | 205 |     |     |     |     |     | 210 |

| TAT | GAG | CTT | GTG | CCT | CCA | CCT | CAT | CAA | TTT | GAT | ACT | CGA | AAC | TAT | TTA | 787 |
|---|---|---|---|---|---|---|---|---|---|---|---|---|---|---|---|---|
| Tyr | Glu | Leu | Val | Pro | Pro | Pro | His | Gln | Phe | Asp | Thr | Arg | Asn | Tyr | Leu |     |
|     |     |     |     | 215 |     |     |     | 220 |     |     |     |     |     | 225 |     |     |

| CAA | GTT | AAT | GGT | TTG | CAA | ACC | AAC | AAC | CAT | TAC | ACT | AGA | CAA | GAC | CAA | 835 |
|---|---|---|---|---|---|---|---|---|---|---|---|---|---|---|---|---|
| Gln | Val | Asn | Gly | Leu | Gln | Thr | Asn | Asn | His | Tyr | Thr | Arg | Gln | Asp | Gln |     |
|     |     |     | 230 |     |     |     |     | 235 |     |     |     |     | 240 |     |     |     |

| CCA | TCT | CTT | CAA | CTA | GTC | TAATATGGTT | GAAAGTCTTC | TATGTTTGT |  |  |  | 883 |
|---|---|---|---|---|---|---|---|---|---|---|---|---|
| Pro | Ser | Leu | Gln | Leu | Val |  |  |  |  |  |  |  |
|     |     |     | 245 |     |     |  |  |  |  |  |  |  |

| GCTCTACATC | TTAACCACAA | GAGAAGACTA | CTATTAAGCC | TGAAGATTCT | TGGAAGTGAA | 943 |
|---|---|---|---|---|---|---|
| GATCAACTTA | ATTATGTATA | CCATATTATA | TTACTTGCTG | AATGAGCTGA | GACTCTTCAA | 1003 |
| TGTTGTATGT | TAAGTGGATA | TGTATTTTTT | AGTTGATGTT | CCTTGTCTGG | CAGTGTACTA | 1063 |
| TGAGGAATTA | CGCTTGTTAT | TATTAAGTTG | ACAACTACTG | TTTATTTTGC | TCAAAAAAAA | 1123 |
| AA |  |  |  |  |  | 1125 |

(2) INFORMATION FOR SEQ ID NO:7:

(i) SEQUENCE CHARACTERISTICS:
        (A) LENGTH: 248 amino acids
        (B) TYPE: amino acid
        (D) TOPOLOGY: linear (ii) MOLECULE TYPE: protein (xi) SEQUENCE DESCRIPTION: SEQ ID NO:7:

|     |     |     |     |     |     |     |     |     |     |     |     |     |     |     |
|---|---|---|---|---|---|---|---|---|---|---|---|---|---|---|
| Met | Asp | Phe | Gln | Ser | Asp | Leu | Thr | Arg | Glu | Ile | Ser | Pro | Gln | Arg | Lys |
| 1 |     |     |     | 5 |     |     |     |     | 10 |     |     |     |     | 15 |

| Leu | Gly | Arg | Gly | Lys | Ile | Glu | Ile | Lys | Arg | Ile | Glu | Asn | Thr | Thr | Asn |
|---|---|---|---|---|---|---|---|---|---|---|---|---|---|---|---|
|     |     |     | 20 |     |     |     |     | 25 |     |     |     |     | 30 |     |     |

| Arg | Gln | Val | Thr | Phe | Cys | Lys | Arg | Arg | Asn | Gly | Leu | Leu | Lys | Lys | Ala |
|---|---|---|---|---|---|---|---|---|---|---|---|---|---|---|---|
|     |     |     | 35 |     |     |     |     | 40 |     |     |     |     | 45 |     |     |

| Tyr | Glu | Leu | Ser | Val | Leu | Cys | Asp | Ala | Glu | Val | Ala | Leu | Ile | Val | Phe |
|---|---|---|---|---|---|---|---|---|---|---|---|---|---|---|---|
|     | 50 |     |     |     |     | 55 |     |     |     |     | 60 |     |     |     |     |

| Ser | Ser | Arg | Gly | Arg | Leu | Tyr | Glu | Tyr | Ala | Asn | Asn | Ser | Val | Lys | Ala |
|---|---|---|---|---|---|---|---|---|---|---|---|---|---|---|---|
| 65 |     |     |     |     | 70 |     |     |     |     | 75 |     |     |     |     | 80 |

| Thr | Ile | Glu | Arg | Tyr | Lys | Lys | Ala | Cys | Ser | Asp | Ser | Ser | Asn | Thr | Gly |
|---|---|---|---|---|---|---|---|---|---|---|---|---|---|---|---|
|     |     |     |     | 85 |     |     |     |     | 90 |     |     |     |     | 95 |     |

| Ser | Ile | Ser | Glu | Ala | Asn | Ala | Gln | Tyr | Tyr | Gln | Gln | Glu | Ala | Ser | Lys |
|---|---|---|---|---|---|---|---|---|---|---|---|---|---|---|---|
|     |     |     | 100 |     |     |     |     | 105 |     |     |     |     | 110 |     |     |

| Leu | Arg | Ala | Gln | Ile | Gly | Asn | Leu | Gln | Asn | Gln | Asn | Arg | Asn | Met | Leu |
|---|---|---|---|---|---|---|---|---|---|---|---|---|---|---|---|
|     |     | 115 |     |     |     |     | 120 |     |     |     |     | 125 |     |     |     |

| Gly | Glu | Ser | Leu | Ala | Ala | Leu | Ser | Leu | Arg | Asp | Leu | Lys | Asn | Leu | Glu |
|---|---|---|---|---|---|---|---|---|---|---|---|---|---|---|---|
|     | 130 |     |     |     |     | 135 |     |     |     |     | 140 |     |     |     |     |

| Gln | Lys | Ile | Glu | Lys | Gly | Ile | Ser | Lys | Ile | Arg | Ser | Lys | Lys | Asn | Glu |
|---|---|---|---|---|---|---|---|---|---|---|---|---|---|---|---|
| 145 |     |     |     |     | 150 |     |     |     |     | 155 |     |     |     |     | 160 |

| Leu | Leu | Phe | Ala | Glu | Ile | Glu | Tyr | Met | Gln | Lys | Arg | Glu | Ile | Asp | Leu |
|---|---|---|---|---|---|---|---|---|---|---|---|---|---|---|---|
|     |     |     |     | 165 |     |     |     |     | 170 |     |     |     |     | 175 |     |

| His | Asn | Asn | Asn | Gln | Tyr | Leu | Arg | Ala | Lys | Ile | Ala | Glu | Thr | Glu | Arg |
|---|---|---|---|---|---|---|---|---|---|---|---|---|---|---|---|
|     |     |     | 180 |     |     |     |     | 185 |     |     |     |     | 190 |     |     |

| Ala | Gln | Gln | Gln | Gln | Gln | Gln | Gln | Met | Asn | Leu | Met | Pro | Gly | Ser |
|---|---|---|---|---|---|---|---|---|---|---|---|---|---|---|
|     |     | 195 |     |     |     |     | 200 |     |     |     | 205 |     |     |     |

| Ser | Ser | Tyr | Glu | Leu | Val | Pro | Pro | Pro | His | Gln | Phe | Asp | Thr | Arg | Asn |
|---|---|---|---|---|---|---|---|---|---|---|---|---|---|---|---|
|     | 210 |     |     |     |     | 215 |     |     |     |     | 220 |     |     |     |     |

| Tyr | Leu | Gln | Val | Asn | Gly | Leu | Gln | Thr | Asn | Asn | His | Tyr | Thr | Arg | Gln |
|---|---|---|---|---|---|---|---|---|---|---|---|---|---|---|---|

-continued

| 225 | 230 | 235 | 240 |
|---|---|---|---|
| Asp Gln Pro Ser | Leu Gln Leu Val | | |
| | 245 | | |

What is claimed is:

1. A dicotyledonous plant comprising at least one cell transformed with a vector comprising a plant agamous nucleic acid wherein a portion of the coding region of said agamous nucleic acid contains at least 15 nucleotides encoding a portion of the DNA binding domain extending from amino acid residues 51 through 109 of SEQ ID NO. 2 herein and wherein said plant has an Ag or AP2 phenotype.

2. The plant of claim 1 wherein said vector comprises a promoter operably linked to said agamous nucleic acid.

3. The plant of claim 2 wherein said promoter is other than the promoter naturally associated with said agamous nucleic acid.

4. The plant of claim 3 wherein said promoter comprises a constitutive promoter.

5. The plant of claim 4 wherein said constitutive promoter comprises a cauliflower mosaic virus promoter.

6. The plant of claim 3 wherein said promoter comprises an inducible promoter.

7. The plant of claim 3 wherein said promoter is a pollen specific promoter.

8. The plant of claim 1 wherein the transcript of said nucleic acid encodes an agamous protein.

9. The plant of claim 8 wherein said phenotype comprises an AP2 phenotype.

10. The plant of claim 1 wherein said agamous nucleic acid is capable of hybridizing under moderate stringency conditions with the agamous nucleic acid of SEQ ID NO. 1, 3 or 6.

11. The plant of claim 10 wherein said phenotype comprises an AG phenotype.

12. The plant of claim 11 wherein said phenotype comprises a double flower.

13. The plant of claim 11 wherein said phenotype comprises a sterile flower.

14. The plant of claim 11 wherein said phenotype comprises a double flower that is sterile.

15. A vector capable of transforming a plant cell to alter floral development in a plant containing said cell, said vector comprising an agamous nucleic acid derived from a plant operably linked to a promoter other than the promoter naturally associated with said agamous nucleic acid, wherein a portion of the coding region of said agamous nucleic acid contains at least 15 nucleotides encoding a portion of the DNA binding domain extending from amino acid residues 51 through 109 of SEQ ID No. 2 herein.

16. The vector of claim 15 wherein said promoter comprises a cauliflower mosaic virus promoter.

17. A vector capable of transforming a plant cell to alter floral development in a plant containing said cell, said vector comprising a plant agamous nucleic acid operably linked in an antisense orientation to a promoter, wherein a portion of the coding region of said agamous nucleic acid contains at least 15 nucleotides encoding a portion of the DNA binding domain extending from amino acid residues 51 through 109 of SEQ ID No. 2 herein.

18. A method for producing a plant having a phenotype characterized by an Ag or AP2 phenotype, said method comprising the steps of:

transforming plant cells with a vector comprising a promoter operably linked to a plant agamous nucleic acid, wherein a portion of the coding region of said agamous nucleic acid contains at least 15 nucleotides encoding a portion of the DNA binding domain extending from amino acid residues 51 through 109 of SEQ ID No. 2 herein;

regenerating plants from one or more of the thus transformed plant cells; and selecting at least one plant having said phenotype.

19. The method of claim 18 wherein said promoter comprises a cauliflower mosaic virus promoter.

20. A dicotyledonous plant produced according to the method of claim 18.

21. The plant of claim 1 wherein a portion of the coding region of said agamous nucleic acid contains nucleotides encoding the DNA binding domain extending from amino acid residues 51 through 109 of SEQ ID No. 2 herein.

22. The vector of claim 15 wherein a portion of the coding region of said agamous nucleic acid encodes the DNA binding domain extending from amino acid residues 51 through 109 of SEQ ID No. 2 herein.

23. The vector of claim 17 wherein a portion of the coding region of said agamous nucleic acid encodes the DNA binding domain extending from amino acid residues 51 through 109 of SEQ ID No. 2 herein.

24. The method of claim 18 wherein a portion of the coding region of said agamous nucleic acid encodes the DNA binding domain extending from amino acid residues 51 through 109 of SEQ ID No. 2 herein.

25. A transformed dicotyledonous plant cell containing the vector of claims 15, 16, 17, 22 or 23.

* * * * *